US008996570B2

(12) United States Patent
Stratman et al.

(10) Patent No.: US 8,996,570 B2
(45) Date of Patent: Mar. 31, 2015

(54) HISTOLOGY WORKFLOW MANAGEMENT SYSTEM

(75) Inventors: Curtis Stratman, Pittsburgh, PA (US); Mark Lotter, Pittsburgh, PA (US); Martin Shelly, Pittsburgh, PA (US)

(73) Assignee: Omnyx, LLC, Pittsburgh, PA (US)

( * ) Notice: Subject to any disclaimer, the term of this patent is extended or adjusted under 35 U.S.C. 154(b) by 0 days.

(21) Appl. No.: 13/233,372

(22) Filed: Sep. 15, 2011

(65) Prior Publication Data

US 2012/0072452 A1 Mar. 22, 2012

Related U.S. Application Data

(60) Provisional application No. 61/383,597, filed on Sep. 16, 2010.

(51) Int. Cl.
| | | |
|---|---|---|
| *G06F 17/00* | (2006.01) | |
| *G06F 19/00* | (2011.01) | |
| *G06Q 10/06* | (2012.01) | |

(52) U.S. Cl.
CPC ............ *G06F 19/366* (2013.01); *G06Q 10/06* (2013.01)
USPC ............................ 707/772; 382/128; 600/562

(58) Field of Classification Search
USPC ................................................ 707/705–783
See application file for complete search history.

(56) References Cited

U.S. PATENT DOCUMENTS

| | | | |
|---|---|---|---|
| 5,793,969 A * | 8/1998 | Kamentsky et al. .......... 709/213 |
| 6,396,941 B1 | 5/2002 | Bacus et al. | |
| 6,847,729 B1 | 1/2005 | Clinch et al. | |
| 7,216,081 B1 * | 5/2007 | Sage ............................ 704/258 |
| 7,970,197 B2 | 6/2011 | de la Torre-Bueno et al. | |
| 2002/0021828 A1 | 2/2002 | Papier et al. | |
| 2003/0110178 A1 | 6/2003 | Woods | |
| 2003/0120633 A1 | 6/2003 | Torre-Bueno | |
| 2003/0163031 A1 | 8/2003 | Madden et al. | |
| 2006/0159325 A1 * | 7/2006 | Zeineh et al. ................. 382/128 |
| 2007/0025606 A1 | 2/2007 | Gholap et al. | |
| 2007/1400540 * | 2/2007 | McLaren et al. ............. 382/128 |
| 2007/0172100 A1 * | 7/2007 | Lefebvre ...................... 382/128 |
| 2008/0137938 A1 | 6/2008 | Zahniser | |
| 2008/0273788 A1 | 11/2008 | Soenksen et al. | |

(Continued)

FOREIGN PATENT DOCUMENTS

WO 2008156566 A1 12/2008

OTHER PUBLICATIONS

International Searching Authority, Search Report for International Application PCT/US2011/051850, Dec. 26, 2011 (EPO), 2 pages.

(Continued)

*Primary Examiner* — Tony Mahmoudi
*Assistant Examiner* — Tuan-Khanh Phan
(74) *Attorney, Agent, or Firm* — Duane Morris LLP

(57) ABSTRACT

Systems, methods, and products are described that provide for a histology workflow management system and associated functions. One aspect provides for accessing one or more digital specimen images; generating one or more patient records and one or more case records; matching the one or more digital specimen images to the one or more case records based on one or more image properties of the one or more digital specimen images; and facilitating one or more image review functions comprising image quality, case matching, tissue block matching, and case completeness functions. Other aspects and embodiments are also described herein.

31 Claims, 22 Drawing Sheets

(56) References Cited

U.S. PATENT DOCUMENTS

| | | | |
|---|---|---|---|
| 2009/0041329 | A1 | 2/2009 | Nordell et al. |
| 2009/0222746 | A1 | 9/2009 | Chirica et al. |
| 2009/0226065 | A1 | 9/2009 | Chen |
| 2009/0234671 | A1 | 9/2009 | Jones et al. |
| 2010/0054574 | A1 | 3/2010 | Marcelpoil et al. |
| 2011/0060766 | A1 | 3/2011 | Ehlke et al. |
| 2011/0129133 | A1* | 6/2011 | Ramos et al. ............ 382/128 |

OTHER PUBLICATIONS

Website, available at http://web.archive.org/web/20100420064246/http://www.aperio.com/pathology-services/SpectrumPlus-information-management.asp, MANAGE-Improve the Quality and Efficiency of Your Pathology Services, 2 pages, Apr. 20, 2010.

Website, available at http://web.archive.org/web/20100630010945/http://www.bioimagene.com/products_solutions/application_software/virtuoso_software.html, Virtuoso, 1 page, Jun. 30, 2010.

Website, available at http://web.achive.org/web/20100728065905/http://www.sunquestinfo.com/Products/Pages/DigitalPathology.aspx, Digital Pathology. 1 page, Jul. 28, 2010.

European Supplemental Search Report and Opinion, dated Jan. 15, 2014 in application No. 11825986.0.

* cited by examiner

Add a Case

Create a case record for your new patient — 1201

NAME: Smith, John — 1202
MRN(S): SY-13ADBJAL1 — 1203
ACCESSIONING: ABC09-1897 — 1204
ACCESSIONING DATE: 06 03 2009 — 1205
PATHOLOGIST: Williams, Mark MD — 1206
NEW - ADD PATHOLOGIST INFO
ORDERING PHYSICIAN: Young, Sarah MD — 1207
CLINICAL HISTORY: The patient has a family history of melanoma. the previous punch biopsies were reported as a negative for Hemangioma — 1208
DIFFERENTIAL DIAGNOSIS: Hemangioma, Seborrhetic keratosis, Traumatized or irritated Nevus, Hemangioma — 1209
GROSSING NOTES: — 1210

< BACK    NEXT >    FINISH

HISTOLOGY WORKFLOW MANAGEMENT SYSTEM

CROSS REFERENCE TO RELATED APPLICATION

This application claims the benefit of U.S. Provisional Patent Application Ser. No. 61/383,597, entitled "Histology Workflow Management System," filed on Sep. 16, 2010, the contents of which are incorporated by reference as if fully set forth herein.

BACKGROUND

Pathology involves the study and diagnosis of disease through the examination of bodily specimens, including tissue, organs, and fluids. Specimens are typically processed into glass microscopic slides through a series of histological procedures, such as fixing, embedding, sectioning, and staining. Typically, a pathologist manually views the microscopic slides under an optical microscope. Alternatively, the microscopic slides may be scanned and digitized for viewing on a display device.

BRIEF SUMMARY

In summary, one aspect provides a system comprising: one or more processors; a memory in operative connection with the one or more processors; wherein, responsive to execution of program instructions accessible to the one or more processors, the one or more processors are configured to: access one or more digital specimen images; generate one or more patient records and one or more case records; match the one or more digital specimen images to the one or more case records based on one or more image properties of the one or more digital specimen images; and facilitate one or more image review functions comprising image quality, case matching, tissue block matching, and case completeness functions.

Another aspect provides a method comprising: accessing one or more digital specimen images; generating one or more patient records and one or more case records; matching the one or more digital specimen images to the one or more case records based on one or more image properties of the one or more digital specimen images; and facilitating one or more image review functions comprising image quality, case matching, tissue block matching, and case completeness functions.

A further aspect provides a computer program product comprising: a computer readable storage medium having computer readable program code embodied therewith, the computer readable program code comprising: computer readable program code configured to access one or more digital specimen images; computer readable program code configured to generate one or more patient and one or more case records; computer readable program code configured to match the one or more digital specimen images to the one or more case records based on one or more image properties of the one or more digital specimen images; and computer readable program code configured to facilitate one or more image review functions comprising image quality, case matching, tissue block matching, and case completeness functions.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 9 provides an example user interface presenting a case status view.

FIG. 10 provides an example of designating the delay status of a slide or digital specimen image.

FIG. 12 provides an example user interface for creating a case record.

DETAILED DESCRIPTION

Figure 1:
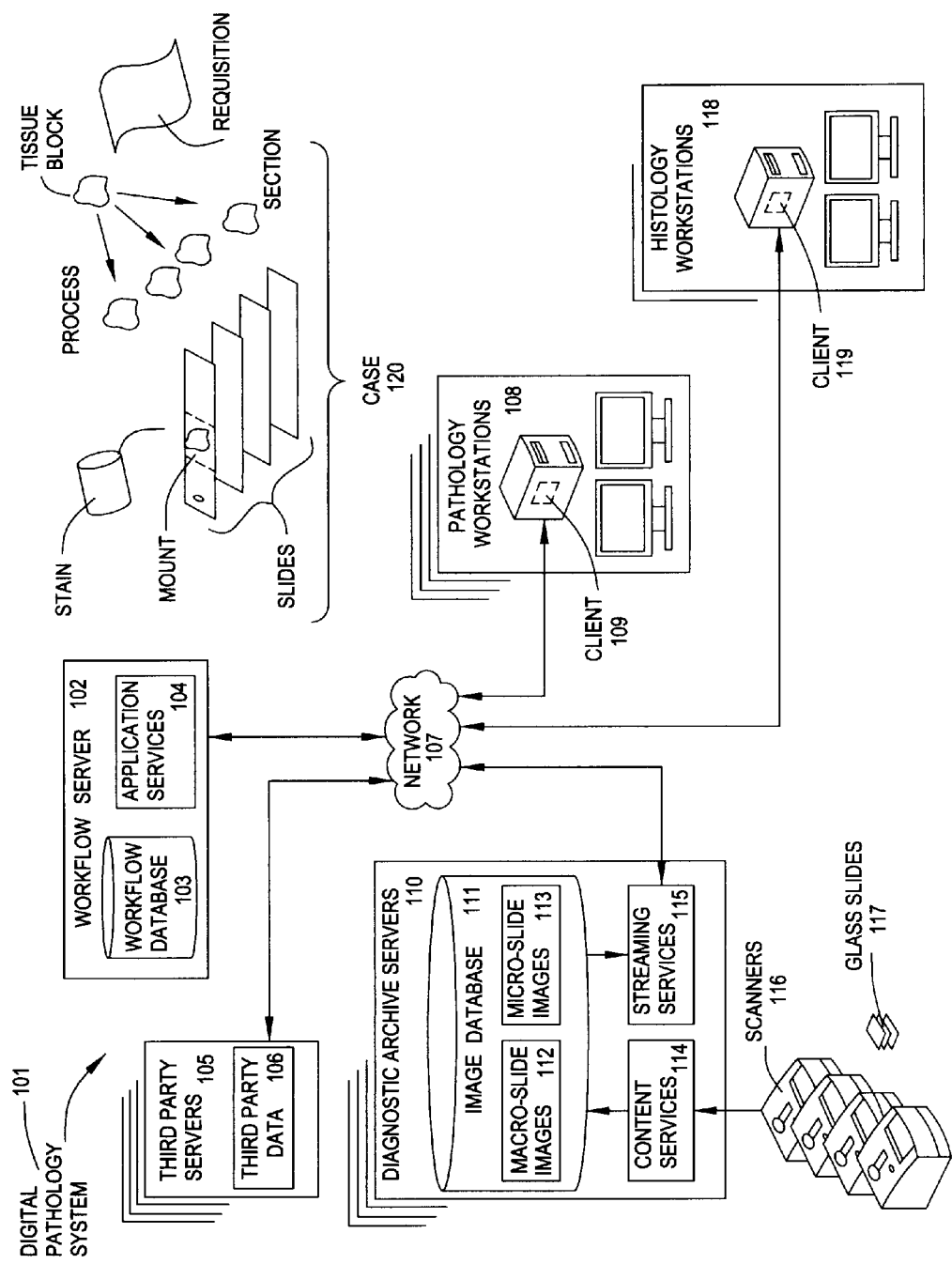
FIG. 1 provides an example histology workflow management system integrated with a digital pathology system.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail to avoid obfuscation.

The medical "case" is the typical pathology functional unit. A case is generally comprised of a patient, a medical concern, specimens derived from samples removed from the patient, and associated data. Each case is assigned a unique identifier, customarily in the form of a file or case number. Prior to being examined by a pathologist, the specimens, such as tissue samples, are prepared on glass slides in a histology laboratory. The slides are prepared through a sequence of connected operations, commonly referred to as the histology workflow. A case typically contains multiple slides that may be labeled with one or more identifiers, such as a case identifier or a unique slide identifier.

In a typical histology workflow, an initial step in processing specimens is grossing, wherein the specimens are dissected, grouped into cassettes, and defined into one or more slide orders. The pieces of dissected tissue may also be referred to as "tissue dice" and are organized into one or more cassettes. The specimens are chemically processed in preparation for being incorporated into microscopic slides. After being chemically processed, a cassette is embedded by orientating and encasing all contained tissue dice into a paraffin wax "block." The blocks are then cut into "sections," typically using a microtome. These sections are subsequently mounted flat on a glass microscope slide.

The slides are stained to provide contrast and to highlight features of interest. The following are three main categories of stains: hematoxylin and eosin (H&E), histochemical (special), and immunohistochemical (IHC). After being stained, a glass or plastic cover slip is typically mounted over the tissue sections to protect the slides.

Control samples are often created for special and IHC stains. A positive control is used to confirm the functionality of a stain batch, for example, to prevent false negatives resulting from stain failures. Tissue from a known positive sample (not from the case) is often used to create the control sample. For example, a positive control may consist of a piece of positive control tissue located on a corner of a prepared slide. The positive control tissue is usually demarcated, such as being outlined with a marker. Alternatively, a separate positive control slide may be used to detect false negatives. Negative controls are also used, mainly to prevent false positives. To create a negative control slide, tissue from the case is processed using the same staining process minus a particular component, such as the IHC stain antigen for an IHC stain control. Contrary to positive controls, negative controls must be created on separate slides.

Certain surgical procedures require an interoperative diagnosis that involves the immediate examination of specimens by a pathologist. These diagnoses may impact future actions in a procedure that is in process and are therefore time critical, typically requiring a preliminary diagnosis in an extremely short time frame, such as ten minutes or less. These time constraints do not allow for processing according to the typical histology workflow. Instead, pathologist typically examine frozen sections, wherein the sample is frozen, processed onto a slide, and reviewed in a space adjacent to the operating room.

According to existing technology, slides, including those made during frozen section processing, are assembled by case and sorted by delivery location. In general, this step is performed manually by a histologist or lab technician by reading the information on the glass slide label, matching the case identifier, and placing the slides next to each other in a tray. In addition, associated paperwork, data, and information contained within a Laboratory Information System (LIS) may provide further details about the case and patient history. Such information may be combined with the slide tray to form a case package for review by a pathologist. It is important that pathologists review all slides and associated information comprising a case before rendering a final diagnosis. Accordingly, it is paramount that laboratory personnel verify completeness or communicate requirements for additional slides, if necessary, before releasing a case.

Quality assurance checks are also an integral part of the histology workflow and pathology diagnosis processes. These checks are typically performed before a case may be released and operate to ensure the quality of the slides and the integrity of the case. Illustrative and non-restrictive examples of quality assurance checks include examining for a proper match between the slide label and the tissue placed on the slide, quality of tissue processing, and proper staining. These checks are typically performed manually by visually looking at the case in the tray or by visually examining slides under a microscope.

Methods for manually performing case assembly and quality assurance with physical glass slides within conventional histological environments are presently known. Advances in existing technology have produced digital image based pathology slides wherein traditional glass slides are replaced by digital specimen images. In general, digital specimen images refer to digitized images of physical microscope slides, while "slides" refer to the physical microscope slides or to software or graphical interface elements representing physical microscope slides. As such, the terms digital specimen image, digital image, digital slide, and scanned slide may be considered synonymous and used interchangeably herein. An exemplary digital pathology system utilizing digital specimen images has been disclosed in U.S. patent application Ser. No. 12/554,276, filed on Sep. 4, 2009, the contents of which are incorporated by reference as if fully set forth herein.

Embodiments provide for a histology workflow management system configured to provide automated administration of histology laboratory functions. Illustrative and non-restrictive examples of histology laboratory functions administered according to embodiments include accessing and viewing digital specimen images, case package assembly and delivery, case status monitoring, histology laboratory activity monitoring, quality assurance checks, and LIS integration. According to an embodiment, the histology workflow management system provides functionality for matching scanned slides to physical slides and reviewing scanned slides for accuracy, for example, before submitting to a pathologist for diagnosis. Embodiments are configured to automatically match slides and digital specimen images to a case and, when slides or digital specimen images are not automatically matched, to provide functionality for efficient alternative methods for matching slides or digital specimen images to a case. In an exemplary embodiment, automatic matching of slides and digital specimen images to cases is facilitated through enhanced identification processes, including, but not limited to the use of bar-coded and RFID labeled slides.

Referring to FIG. 1, therein is depicted an example histology workflow management system integrated within a digital pathology system according to an embodiment. A digital pathology system 101 is provided that comprises a workflow server 102, one or more third party servers 105, one or more diagnostic archive servers 110, and pathology workstations 108 arranged in a network 107. A functional unit of the digital pathology system may be the case 120, which may be comprised of, inter alia, specimen slides and a requisition. According to embodiments, histology workflow management functions may be performed through one or more digital histology workstations 118 operatively coupled to the network 107 and running a digital histology application client 119.

Digital specimen images may be generated by scanning prepared glass slides 117 using scanners 116 capable of transforming glass specimen slides into digital specimen images. As shown in FIG. 1, the digital specimen images may be stored on a diagnostic archive server 110 in an image database 111. A content services module 114 may be utilized to manage the acquisition of digital specimen images, including macro-slide images 112 and micro-slide images 113. The outbound flow of digital specimen images to the network 107 may be managed through one or more streaming services 115. Digital specimen images may be accessed from an image database 111 through digital pathology workstations 108 running a digital pathology application client 109 or through a digital histology workstation 118 running a digital histology application client 119. The digital pathology application client 109 or digital histology application client 119 may provide navigation tools allowing a user, such as a pathologist, to view and manipulate digital slide images.

Third party data 106, such as data available through a general Laboratory Information System (LIS) or a specialized Anatomic Pathology Laboratory Information System (APLIS), may be integrated with the digital specimen images. As illustrated in FIG. 1, the third party data 106 may be supplied through third party servers 105 operatively connected to the network 107.

In FIG. 1, a workflow server 102 is provided that hosts application services 104 for supporting one or more workstations 108, 118 operatively connected through a network 107. The workflow server 102 also includes a workflow database 103 for storing data, including, but not limited to case data and information related to the digital pathology system, such as image catalog information for identifying the image server that is the source of the digital specimen images. One or more application services 104 may be operational on the workflow server 102. According to embodiments, application services 104 may include functions directed toward assigning cases, managing case information and access thereto, cataloging images stored on the diagnostic archive servers 110, and providing reporting mechanisms.

Digital histology workstations 118 may be configured according to embodiments to enable histology functions using digital specimen images, manage histology data entry and generation, and to manage histology workflow process control. As demonstrated in FIG. 1, digital histology workstations 118 may be operatively connected to a network 107, which provides access to data including, but not limited to, digital specimen image files, patient information, case and case package information, and medical personnel information. Residing at and executing on each digital histology workstation 118 is a digital histology application client 119. Embodiments provide that the digital histology application client 119 may be operatively connected to network 107 components, including, but not limited to, the workflow server 102, third party servers 105, pathology workstations 108, and diagnostic archive servers 110, and may access files and data stored thereon. According to embodiments, the concerted operation of application services 104 and the digital histology application client 119 function to support a histology workflow software module (not shown) and digital specimen image viewer software module (not shown).

A histology workflow software module configured according to embodiments facilitates automated histology workflow processes and case management. Non-limiting examples of supported functions include case package assembly and quality assurance checks of digital specimen images and associated data. The histology workflow module provides a set of functions that histologists conventionally perform manually using physical case packages comprised of glass slides and paper-based information. Embodiments provide that the histology workflow module may be comprised of one or more workflow visual elements, for example, workflow menus. The workflow menus may be configured according to embodiments to enable certain functions, including, but not limited to, viewing lists of digital specimen images awaiting case assembly, viewing digital specimen images awaiting quality assurance checks, viewing cases awaiting assembly of digital specimen images or quality assurance checks, viewing cases and digital specimen images during quality assurance checks, and performing actions to address identified quality assurance issues.

Figure 2:
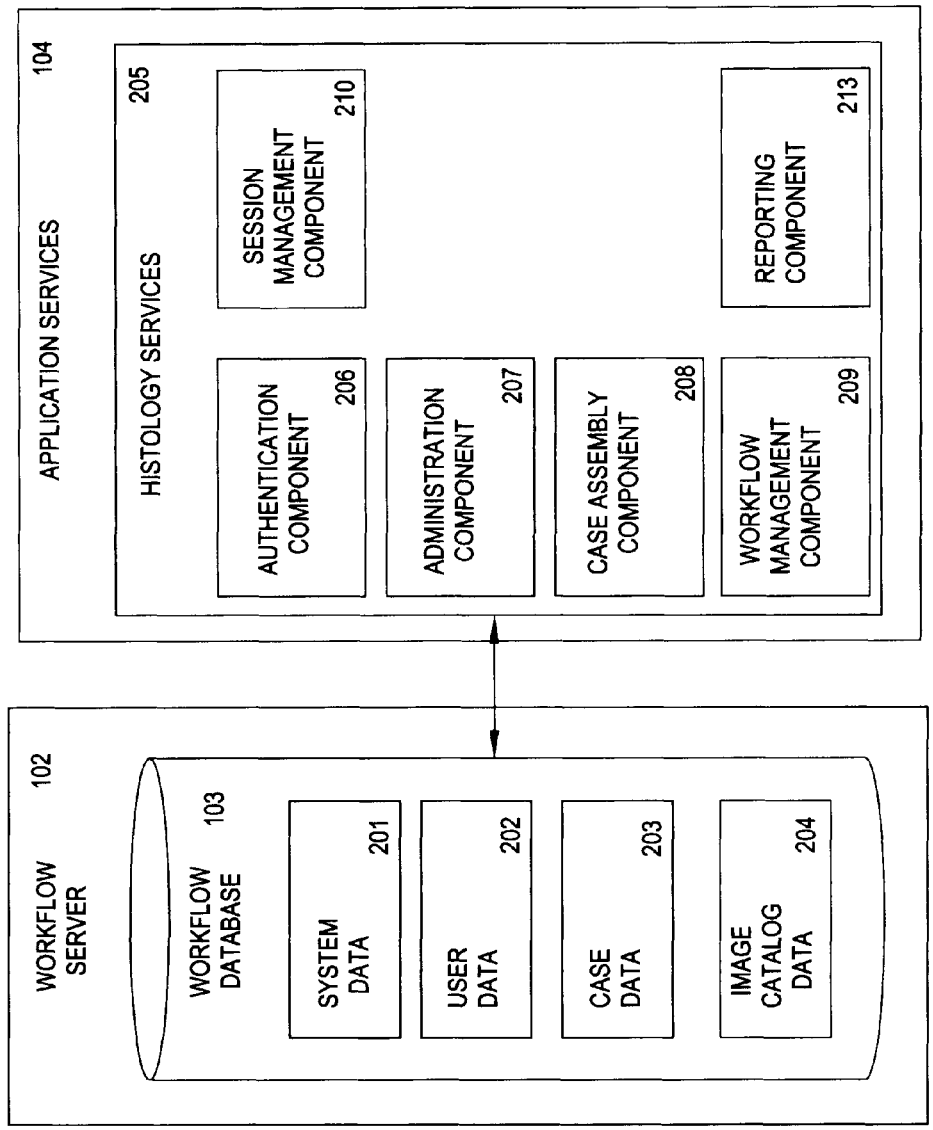
FIG. 2 provides an example histology services application operating on a workflow server.

FIG. 2 illustrates an example histology services application operating on a workflow server. Embodiments provide that system application services 104 may be comprised of one or more histology services application 205 operatively in communication with a workflow database 103 running on a workflow server 102. As illustrated in FIG. 2, a histology services application 205 may be comprised of components including, but not limited to, an authentication component 206, an administration component 207, a case assembly component 208, a workflow management component 209, a session management component 210, and a reporting component 213. In addition, FIG. 2 also illustrates that the information stored in a workflow database 103 of workflow server 102 may be comprised of data such as system data 201, user data 202, case data 203, and image catalog data 204.

The authentication component 206 illustrated in the example of FIG. 2 may be a software component for authenticating users and controlling data access rights. For example, an authentication component configured according to embodiments may be used to maintain records of authorized user names, user IDs, user passwords, user locations, names of laboratories associated with each user, and the like, which may be accessed during a histology workflow management system login. Additionally, the authentication component 206 may be used to maintain records of entities authorized to exchange information with components of the histology workflow management system. For example, the authentication component 206 may be used to maintain records of authorized diagnostic archive servers 110, workstations 108, 118, and third party servers 105. User and/or entity information that is processed by the authentication component 206 may be stored, for example, as system data 201 and/or user data 202 in the workflow database 103. Additionally, system data 201 may include, for example, security data, usage data, billing information, and the like.

The administration component 207 may be comprised of a software component providing administrators with the ability to add, update, and/or remove authorized users and/or entities of the histology workflow management system. For example, the administration component 207 may be used to process records of users and/or entities of the authentication component 206. The administration component 207 may also be used by administrators to manage the assignment of medical cases to users (e.g., pathologists, histologists, or laboratory technicians) and/or to monitor the status of assigned medical cases.

As shown in FIG. 2, the histology services application 205 may comprise a case assembly component 208, configured from one or more software elements to associate all information relating to each medical case. A non-limiting example provides that for a medical case associated with a certain patient, the case assembly component 208 may be used to associate case data 203 for the case with the macro-slide images 112 and/or micro-slide images 113 that belong to the case. The case assembly component 208 may operate to assemble case information to form a case, for example, by linking case data elements together. The source of case data 203 may be, for example, certain third party data 106. In one particular example, case data 203 may be any digital information about a patient of interest (e.g., medical records), the patient's physician, the slides, the case requisition sheet, tissue parts, assigned pathologist, assigned bench, and so on, that may be supplied by an associated information system (e.g., LIS, APLIS).

Streaming sessions (e.g., viewing sessions) may be initiated at a digital histology workstation 118 through the workflow management component 209. In particular, the workflow management component 209 may be used to locate requested macro-slide images 112 and/or micro-slide images 113 of cases being viewed during active workstation sessions. In an illustrative and non-restrictive example, the workflow management component 209 may be used to access and interact with image catalog data 204 when servicing requests for slide image data. Image catalog data 204 may include records of the locations of macro-slide images 112 and micro-slide images 113 stored on system diagnostic archive servers 110. According to embodiments, once a user session has been initiated, the session management component 210 may be used to process requests from and responses to system digital histology workstations 118, and to log session data to/from the workflow database 103, and related functions.

Figure 3:
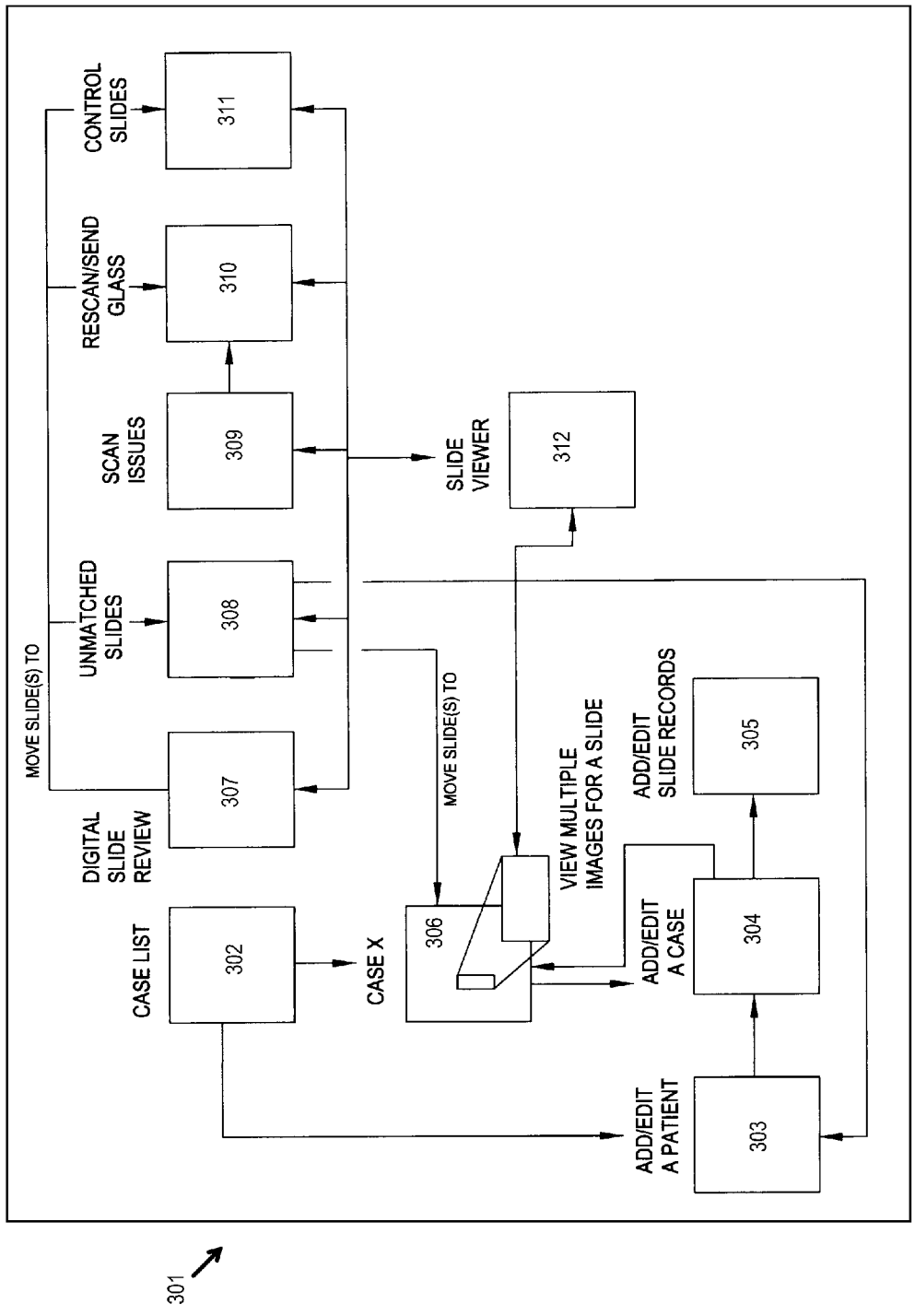
FIG. 3 provides an example of histology workflow management system functions.

Referring to FIG. 3, therein is depicted an example of histology workflow management system functions arranged according to an embodiment. System cases may be managed through one or more case lists 302, which may be configured to provide a summary of all available cases. The case summaries may be comprised of case elements such as priority, accession number, assigned pathologist, assigned bench, case status, and the number of parts and specimens associated with the case. Case records 306 may be accessed and created from the case list 302. This enables users (e.g., pathologists and histologists) to view digital specimen images in a case-centric process. According to embodiments, cases may be edited and created 304 manually through entry of case information and case structure, including parts and blocks. In addition, embodiments provide that data entry, such as data entry relating to patient and case information, may be automated through integration with one or more information systems, such as LIS and APLIS.

Patients may be added or edited 303 from the case list 302, for example, by making an add or edit patient selection from a case list 302 interface. Slide records 305 may be added or edited within the histology workflow management system 301. A slide viewer 312, accessible through the case records 306 or the digital slide review 307, may be utilized to view digital specimen images.

According to embodiments, quality assurance checks may be performed within the histology workflow management system 301 through digital specimen image review 307. Illustrative and non-restrictive examples of quality assurance checks available through the digital specimen image review 307 include image-to-case matching, tissue-to-block matching, and case completeness, which are described in more detail below. Embodiments provide for certain operations, actions, or functions for performing quality assurance checks and for responding to the outcome of same. Non-limiting examples of such operations, actions, or functions depicted in FIG. 3 include unmatched digital specimen images or slides 308, scan issues 309, rescan/send glass 310, and control images or slides 311 operations, described further below.

Embodiments provide that the digital specimen image review 307 may be configured to provide at least the following actions: filtering digital specimen images (e.g., by scanner or histology site); checking digital specimen image quality; ensuring digital specimen images are associated with the correct case; sending digital specimen images to other locations within the histology workflow management system 301 or to external locations (e.g., digital pathology system); deletion of digital specimen images, and requesting the rescanning of associated glass slides.

Digital specimen images configured according to embodiments may be automatically matched to a case. However, certain digital specimen images may not be automatically matched to a case or may have been unmatched from a case, for example, responsive to discovery of an improper match. Accordingly, the histology workflow management system 301 provides for the matching of unmatched digital specimen images. Embodiments may provide access to the group of unmatched digital specimen images 308 and allow for the selection of one or more unmatched digital specimen images for relation to a case record 306, patient 303, or digital specimen image placeholder (not shown). In addition, embodiments provide for searching functionality configured to match unmatched slides or digital specimen images.

A search configured according to embodiments may be based on certain slide or image characteristics, such as stain type, part ID, and full or partial accession number. Slides and images may be matched to cases or patients returned from the search function. For example, a search conducted using the full accession number may return a case with the matching accession number. A search conducted using a partial accession number may return a list of cases matching the partial accession number. This list may be accompanied by a set of options facilitating the location of the case associated with the subject slide or image. Non-limiting examples of options include case, slide, or image characteristics such as the accession number, stain type, block, and part designations.

The digital specimen image review 307 depicted in FIG. 3 allows for a scan issues 309 quality assurance check that involves the examination of the image quality of a digital specimen image. A user may request a rescan of a digital specimen image or delivery of the source glass slide 310, for example, if the image scan is not satisfactory. According to embodiments, requesting a rescan or glass slide 310 may delete the associated digital specimen image. Another quality assurance check available from within digital specimen image review 307 is a control images 311 function that provides access to images of control slides for quality review of digital specimen slides, such as for stain and tissue processing quality. Although described herein in combination with the use of control slides, the stain and tissue processing quality checks may also be performed without control slides.

Figure 4:
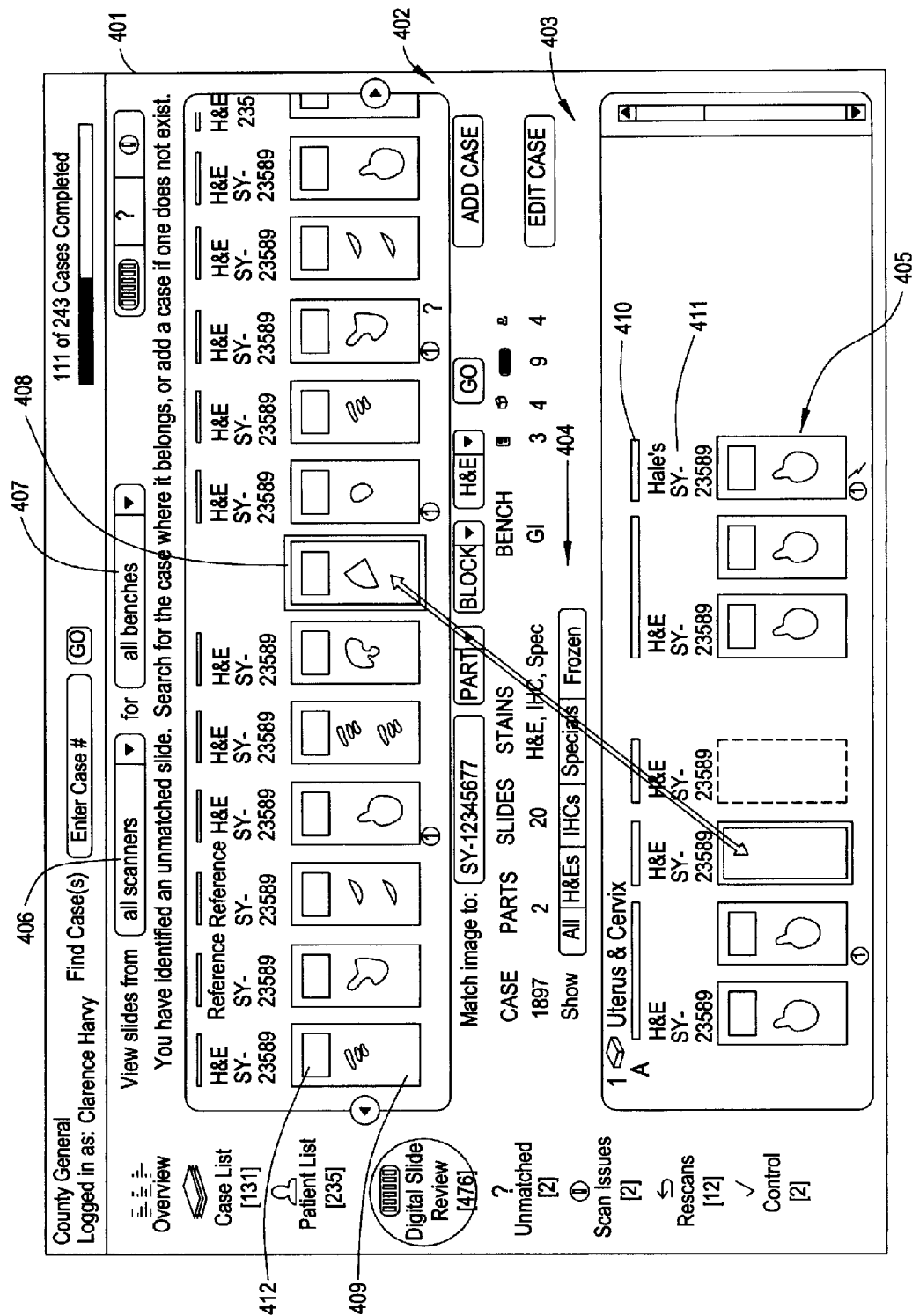
FIG. 4 provides an example user interface displaying digital specimen images prepared for case assembly.

FIG. 4 provides an example histology workflow management system user interface displaying digital specimen images prepared for case assembly according to an embodiment. The user interface screen 401 provides access to available digital specimen images 402 and a case 403. The case 403 depicted in FIG. 4 is comprised of case information 404 and case slide records 405. According to embodiments, a digital specimen image 402 or slide record 405 may be comprised of elements including, but not limited to, a scanned image 409, color bar 410, stain type 411, slide label 412, and bar code (not shown). Embodiments provide that the color bar 410 may be configured to indicate the type of stain on the slide.

As depicted in FIG. 4, a user may search for a case 403 for display in a slide tray format organized by part and block. Filtering mechanisms 406, 407 are also available from the user interface screen 401, such as scanner 406 and bench or laboratory 407 scanning mechanisms, which allow a user to filter the digital specimen images 402 accessible from the screen 401. A non-restrictive example provides that filtering the digital specimen images 402 may allow a user to segment their workload within the same laboratory, between operations within the same laboratory, or even across laboratories. As shown in FIG. 4, an unmatched digital specimen image 408 may be selected and associated with a case 403, for example, by dragging and dropping the image 408 into the case 403 area of the user interface screen 401.

Figure 5:
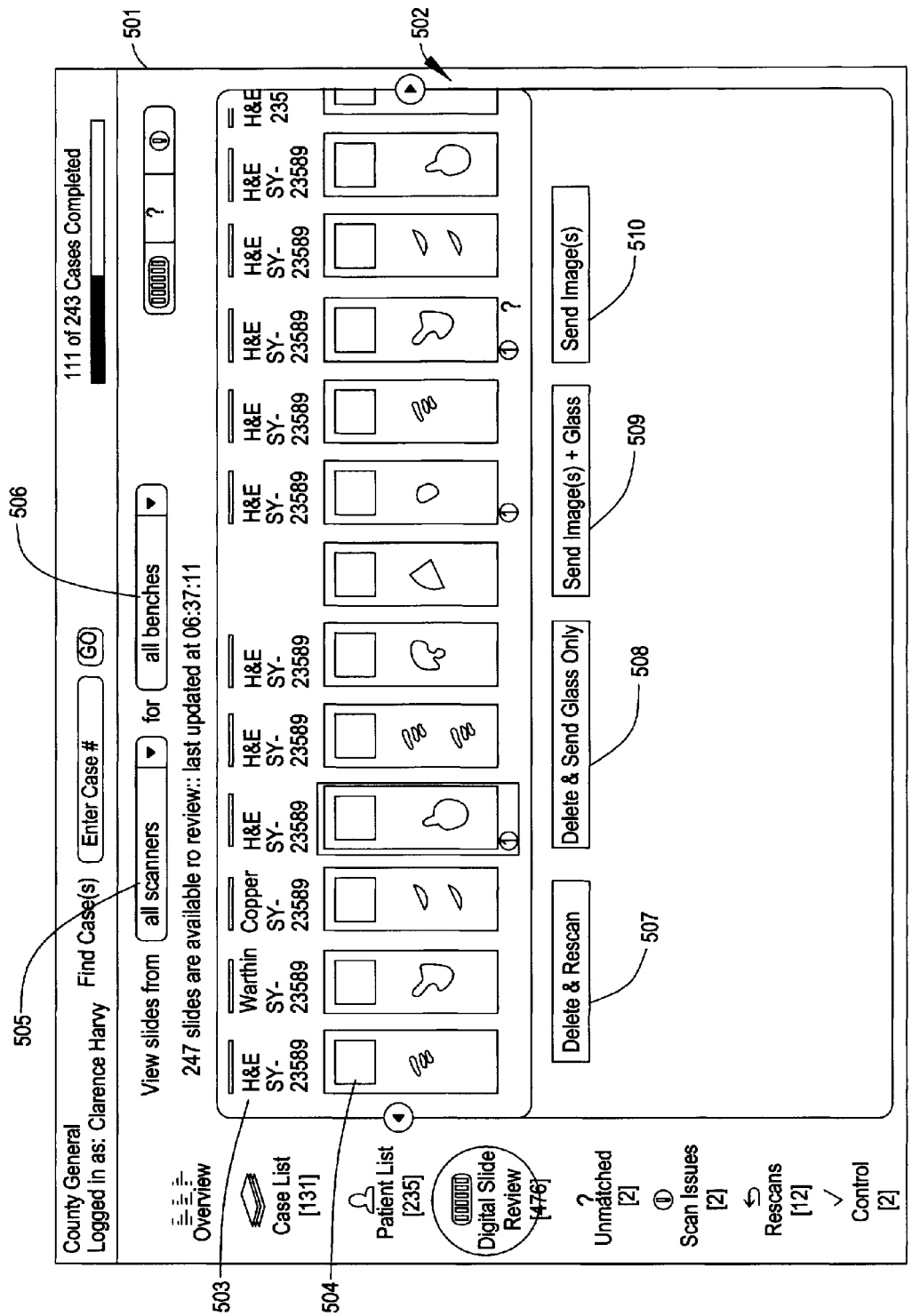
FIG. 5 provides an example user interface providing digital slide images prepared for quality assurance review.

Referring to FIG. 5, therein is depicted an example histology workflow management system user interface providing digital slide images prepared for quality assurance review. One or more digital slide images 502 are made available through the user interface screen 501. According to embodiments, certain identifying information may be placed selectively to facilitate efficient and accurate quality assurance checks. A non-limiting example provided in FIG. 5 comprises the placement of the case accession number and expected label text 503 above the digital slide image label 504. Non-limiting examples of expected label text include, but are not limited to, part, block, stain, and level information. This placement facilitates the quality assurance check of verifying that digital slide images are matched to correct cases (e.g., image-to-case matching).

Filtering mechanisms may also be provided for filtering images based on scanner 505 and bench or laboratory service 506. Filtering images based on bench or laboratory service may allow a user (e.g., histologist) to segment their workload by skill set, and may facilitate prioritization to load balance laboratory output across the pathology or histology department, or a particular location in a multi-facility organization.

Embodiments provide that a user may perform one or more functions on a selected digital specimen image 502 from within the user interface 501, for example, responsive to completion of the quality assurance checks. In the example depicted in FIG. 5, available functions include "Delete & Rescan" 507, "Delete & Send Glass Only" 508, "Send Image(s)+Glass" 509, and "Send Image(s)" 510. In addition, embodiments provide for functions enabling users to send all selected slides or particular slides, such as all slides of a particular stain type (not shown).

Figure 6:
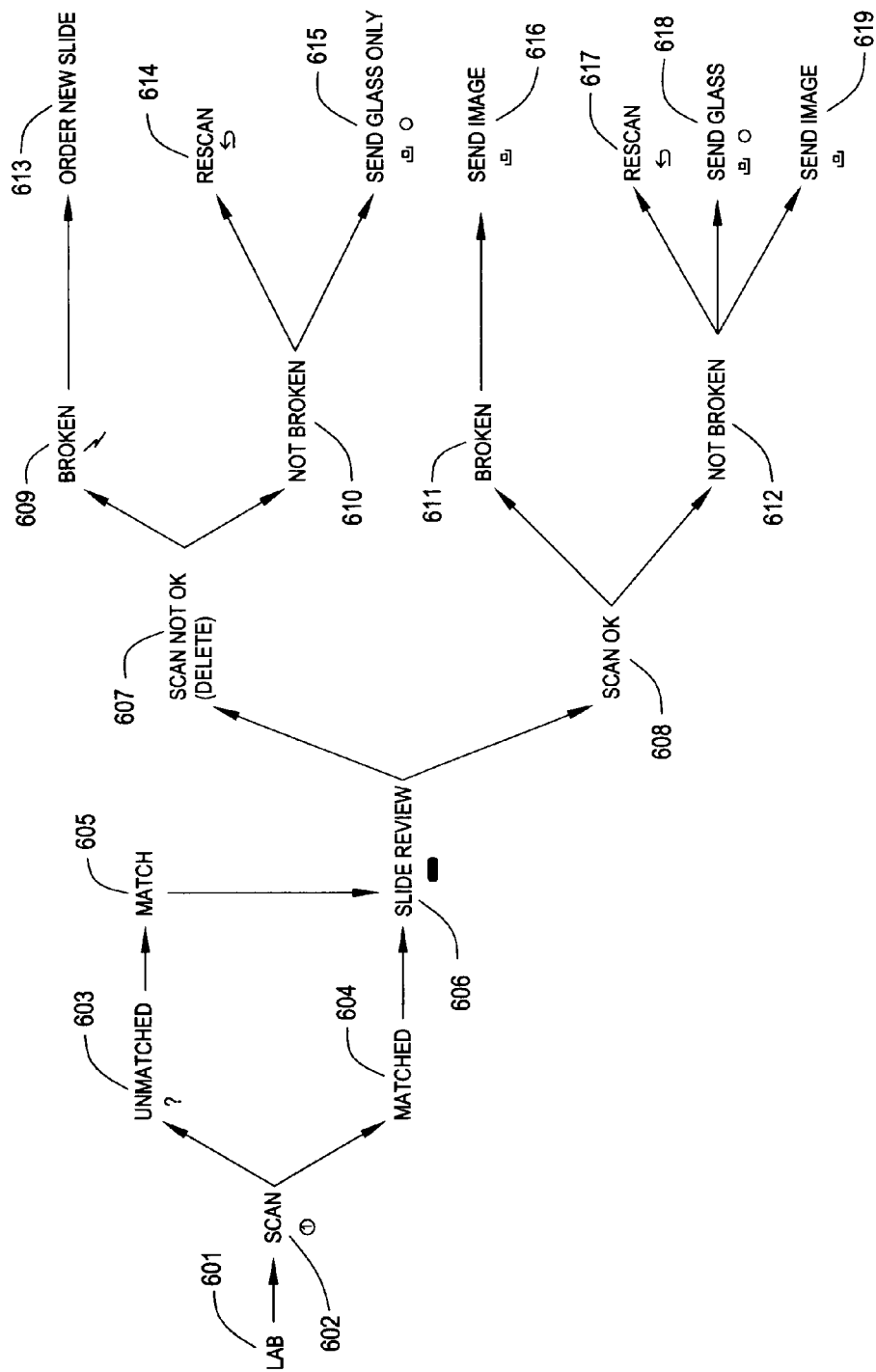
FIG. 6 provides an example process for quality assurance checks and actions on images resulting from quality assurance review.

An example process for quality assurance checks and actions on images resulting from quality assurance review within the histology workflow management system is provided in FIG. 6. According to embodiments, a user may take certain actions as a result of the quality assurance checks, including, but not limited to, sending a digital specimen image to pathologist, deleting an image, marking an associated slide for rescanning, and deleting an image and marking the associated slide for delivery as glass. As shown in FIG. 6, the histology laboratory 601 receives scanned digital specimen images 602, which may be matched to a case 604 or unmatched 604. If an image is unmatched 603, it may be matched 605 with a case according to embodiments described herein. Digital slide images may be subjected to digital slide review 606 functions including, but not limited to, determining whether a scanned image is satisfactory 608 or whether it is not satisfactory and subject to deletion 607. If an image is not satisfactory 607, whether or not the associated slide is broken 609, 610 may be determined. If the associated slide is broken 609, a new slide may be ordered 613; otherwise, if the associated slide is not broken 610, options provide for rescanning 614 the associated slide or for sending the associated glass slide 615.

In the example depicted in FIG. 6, when an image is found to be satisfactory 608, whether or not the associated slide is broken 611 or not broken 612 may be determined. If the associated slide is broken 611, a user may select to send the related image 616. In the alternative, if the associated slide is not broken 612, the slide may be rescanned 617, sent as a glass slide 618, or the related image may be sent 619, for example, to a connected digital pathology system. According to embodiments, the functions and actions provided in FIG. 6 may be realized through various elements, including modules (e.g., software modules), virtual or digital buttons, and interactive interfaces, which operate to carry out the functions and actions within the digital histology workflow management system.

Figure 7:
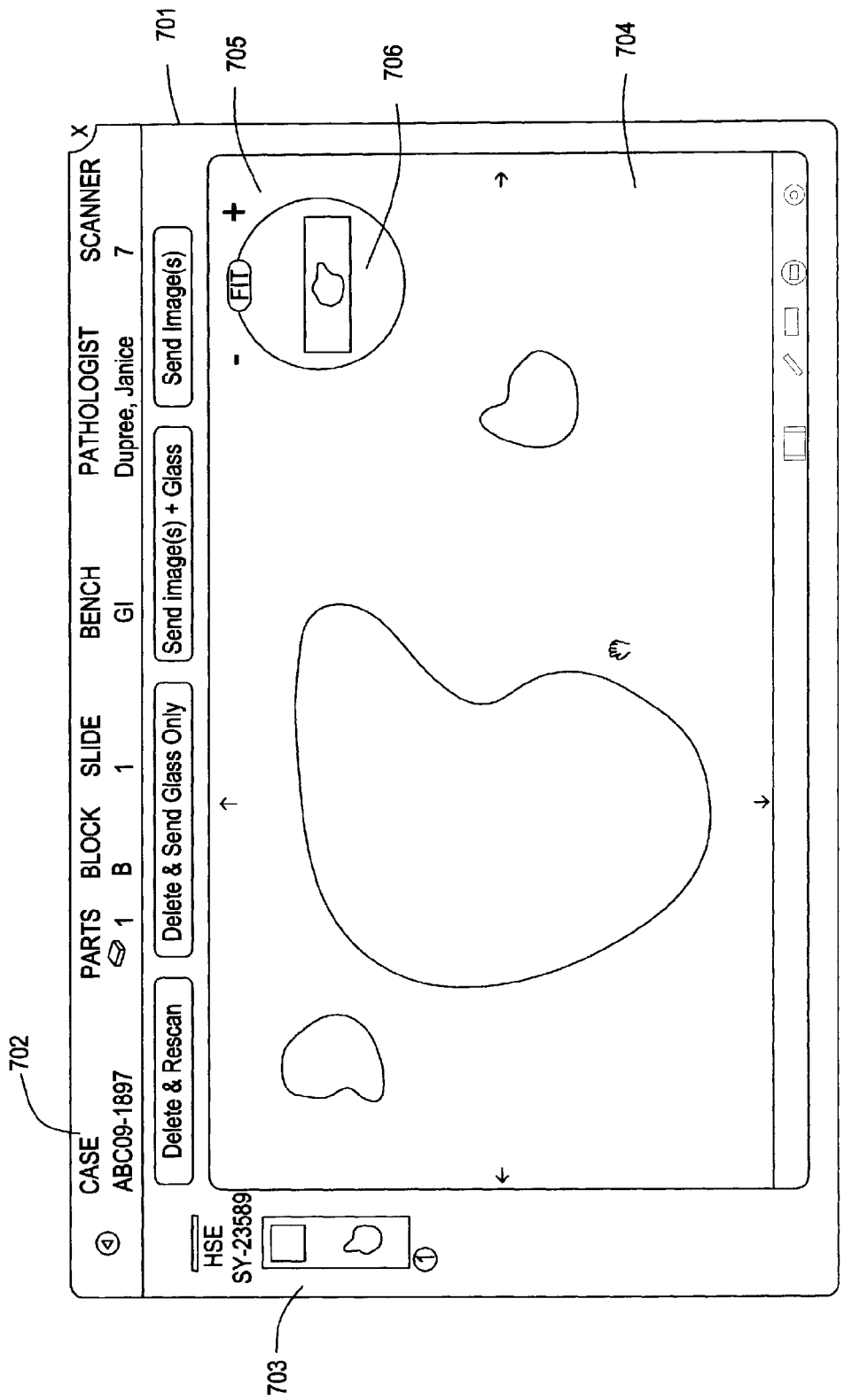
FIG. 7 provides an example user interface for viewing whole slide images.

Embodiments are configured to present whole slide images within the histology workflow management system environment. Referring to FIG. 7, therein is depicted an example system user interface for viewing whole slide images according to an embodiment. Cases 702 and associated digital specimen images 703, 704 may be accessed from the user interface screen 701. A user may navigate a whole digital specimen image 704 using tools available according to embodiments, including, but not limited to, pan and zoom tools. Embodiments provide that viewing and navigating the whole digital specimen image 704 may be utilized, inter alia, to perform quality checks, for example, for tissue preparation quality, stain quality, control tissue staining, and image quality.

According to embodiments, the macroscopic image 703 may be placed on the screen with the whole digital specimen image to facilitate certain quality assurance checks. A non-limiting example of a quality assurance check provides that the placement of the macroscopic image 703, along with its associated accession number and expected label text, facilitates checking whether the macroscopic image 703 showing the label and the whole digital specimen image 704 are properly matched and that all tissue on the associated slide has been captured in the whole digital specimen image 704. In addition, the macroscopic image 703 provides a quick glimpse at which image is currently being viewed as the whole digital specimen image 704, which will assist in navigation through multiple slides. Also depicted in FIG. 7 is the stage view 705 and associated stage view image 706, which may be configured according to embodiments to emulate the stage on a traditional microscope in association with certain tools. Non-limiting examples of tools include zoom, rotation, and location indicator functions.

Figure 8:
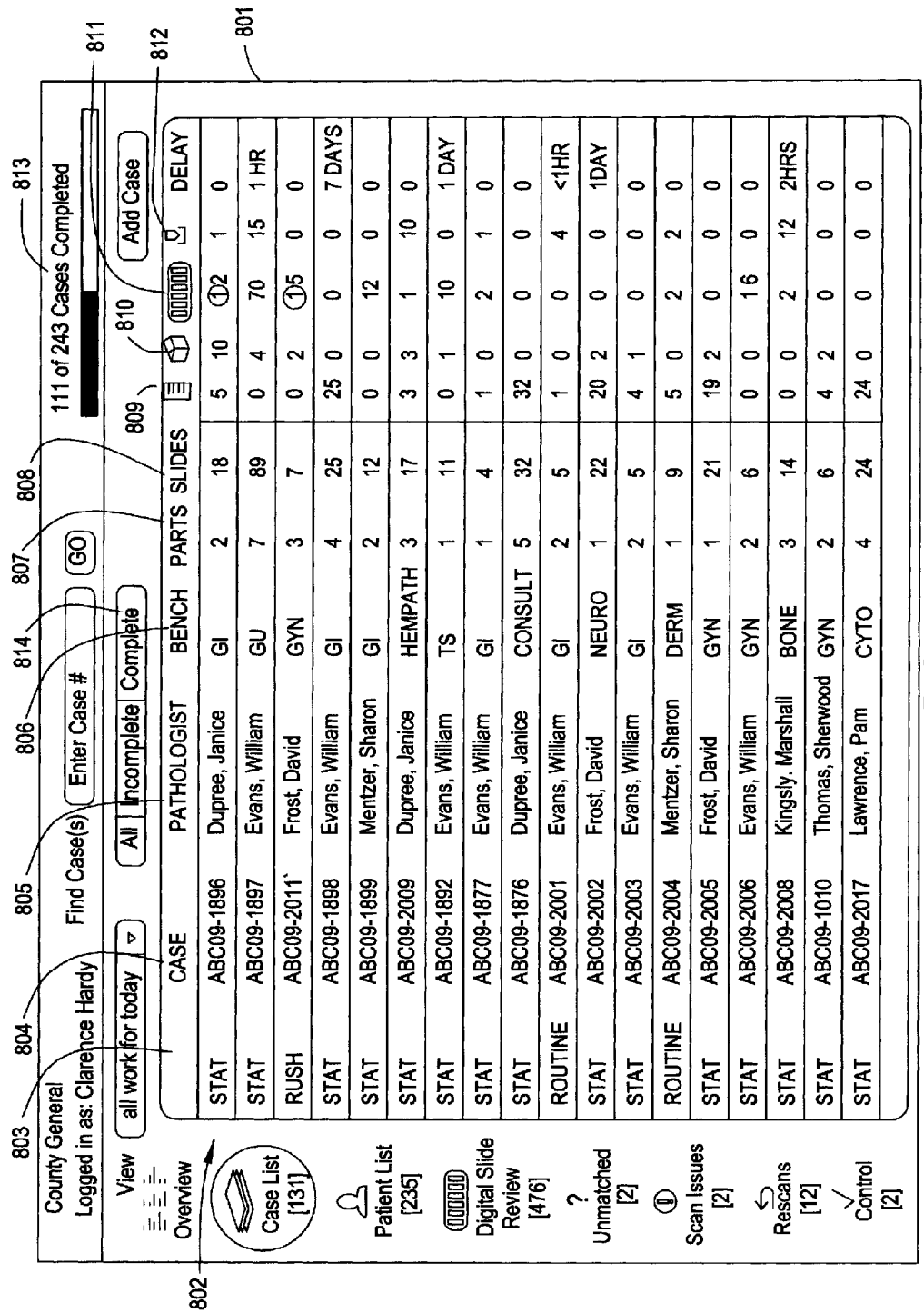
FIG. 8 provides an example user interface presenting a case listing arrangement.

The histology workflow management system disclosed herein provides intuitive and efficient access to cases. In FIG. 8, therein is illustrated an example user interface presenting a case listing arrangement configured according to an embodiment. The user interface screen 801 provides a listing of cases 802 comprised of case elements. In the non-limiting example provided in FIG. 8, the case elements include priority 803, accession number 804, assigned pathologist 805, assigned bench 806, total number of parts 807, total number of slides 808, number of slides awaiting scan 809, number of slides loaded into the scanner 810, number of slides scanned with digital specimen images awaiting quality assurance review 811, and number of slides with digital specimen images released to the pathologist 812. The presentation of cases 802 as depicted in FIG. 8 allows a user, such as a histologist, to track the status of their workload at a case component level. In addition, embodiments provide that the case list may be sectioned, for example, by specialty, to divide items into logical groups.

Conventional histology workflow provides that a case may be considered complete when the number of slides released to the pathologist equals the total number of slides. In FIG. 8, a summary of the number of completed cases out of the total number of cases 813 is provided, as well as a screen element allowing for the selective viewing of cases based on completion status 814. The completed case summary 813 and selective case view based on completion status 814, in conjunction with continual updates reflecting the completion and arrivals of cases, operates to allow a user to constantly monitor system case workload.

Figure 9:
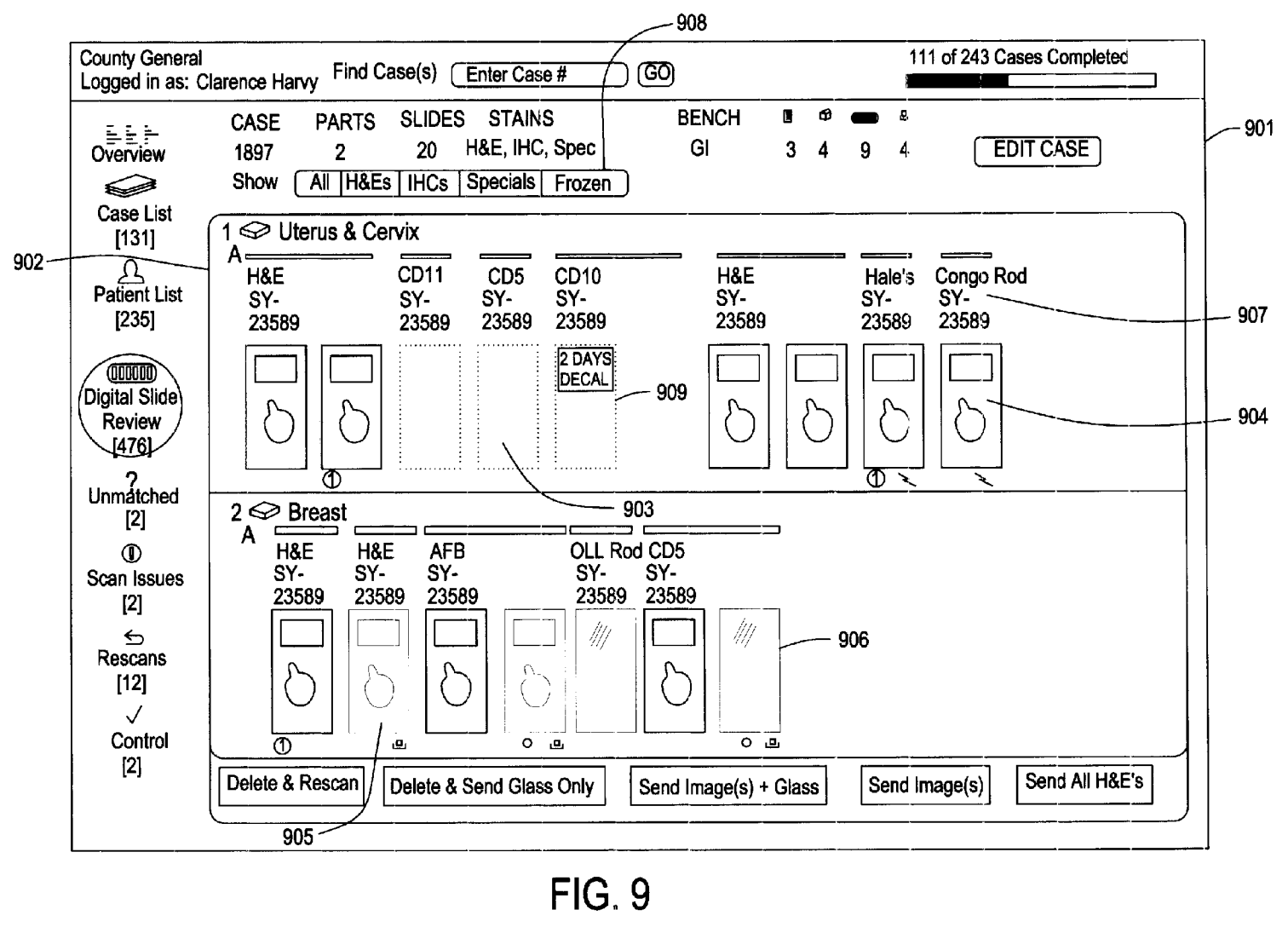

Referring to FIG. 9, therein is depicted an example user interface presenting a case status view configured according to an embodiment. A case status view user interface screen 901 presents a case in a slide tray view 902 and digital specimen images distinguished by status, including, but not limited to, digital specimen images awaiting scanning 903, images awaiting quality assurance review 904, images or slides released to the pathologist 905, images or slides marked to be delivered as glass 906, and a slide marked as delayed 909. Embodiments provide that slides marked to be delivered as glass 906 may be delivered instead of digital images or in addition to digital images.

As illustrated in FIG. 9, slides may be arranged within the slide tray view 902 by part and block. This arrangement may facilitate the quality assurance check of matching tissue size and shape across slides within a block (e.g., tissue-to-block matching). Digital specimen images within the slide tray view 902 may be associated with placeholder indicators 907 that provide additional information, including, but not limited to, the name of the stain positioned below color bars indicating stain type. The presence of digital specimen images awaiting scanning 903 operates to facilitate, inter alia, the case completeness quality assurance check.

The slide tray view 902 may be filtered according to selectable display options 908. In the example illustrated in FIG. 9, the selectable display options comprise stain type; however, other selectable display options are also contemplated. The filtering function operates to enable labs with separate workflows to create digital specimen images for each stain type, focus quality assurance checks to their specific scope, and to send all slides within a particular stain type with a single action.

Figure 10:
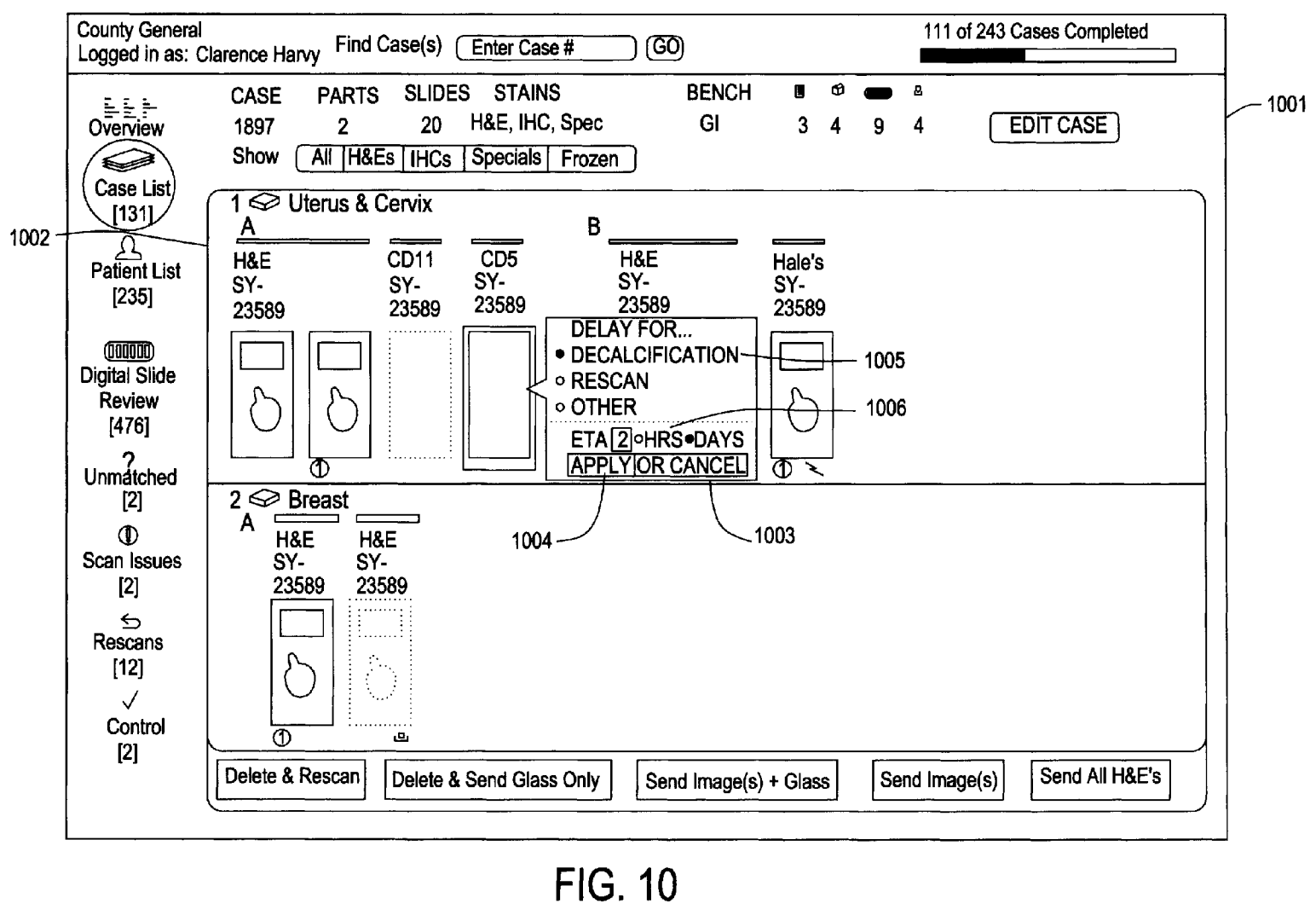

The delivery of slides or digital specimen images from the histology laboratory to the pathologist may be delayed for various reasons, such as decalcification or low image quality. According to embodiments, digital specimen images within the histology workflow management system may be associated with delay information, including, but not limited to, whether a slide is delayed, reasons for the delay, and an estimated time of arrival. In FIG. 10, therein is depicted an example of designating a slide or digital specimen image for delayed delivery according to an embodiment. The user interface screen 1001 presents digital specimen images or slides 1002. A delay interface 1003 may be initiated from the user interface screen 1001 to allow a user to designate a digital specimen image or slide for delayed delivery. The delay interface 1003 may provide selections for specifying the status of a digital specimen image or slide, including, but not limited to, setting the delayed status 1004, reason for delay 1005, and estimated time of arrival 1006.

Embodiments provide that a slide or digital image specimen may be configured to present visual feedback of an applied delay status when displayed on a system user interface. Non-limiting examples of the visual feedback include highlighting and presentation of a delay marker on the related delayed record. According to embodiments, the delay status and associated information of a digital specimen image or slide may be available throughout the histology workflow management system and any operatively connected systems (e.g., a digital pathology system). As such, if a digital slide image is delayed, the information may be accessible to other users attempting to access the image, allowing interested parties (e.g., pathologists) to plan and coordinate accordingly.

Figure 11:
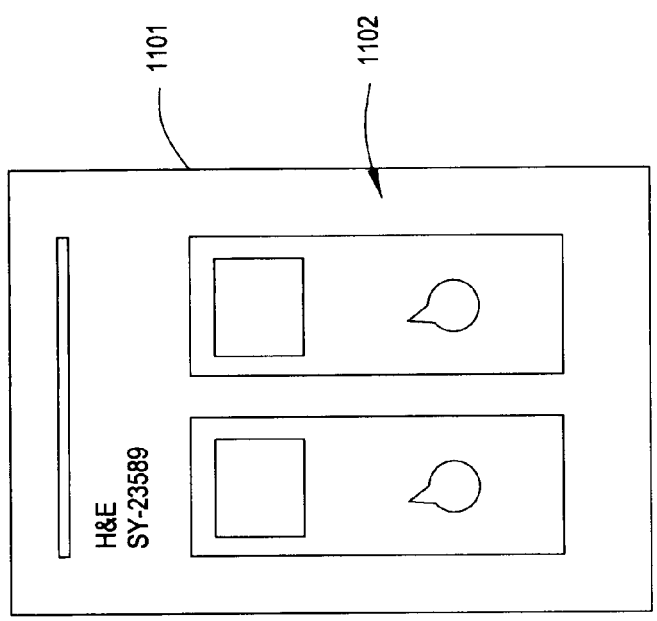
FIG. 11 provides an example physical slide record associated with multiple digital slide images.

Each physical slide may be scanned multiple times, for example, to provide different resolutions. Embodiments may be configured to associate multiple digital specimen slides generated from scanning a slide with a physical slide record. Referring now to FIG. 11, therein is provided an example physical slide record associated with multiple digital slide images according to an embodiment. As shown in FIG. 11, a user accessing a physical slide record may be presented with a user interface 1101 displaying the digital specimen slides 1102 associated with the physical slide record.

Case records may be generated and edited within the histology workflow management system. FIG. 12 illustrates an example user interface for creating a case record according to an embodiment. The same or a similar interface may be used to edit existing cases. An add case interface 1201 provides functionality for adding a new case record. The interface 1201 presents users with data entry elements associated with generating a new case record, including, but not limited to, elements for describing the patient 1202, 1203, associated record numbers 1204, 1205, associated medical personnel or distribution destination designated by medical personnel 1206, 1207, and case descriptors such as clinical history 1208, differential diagnosis 1209, and grossing notes 1210.

Figure 13:
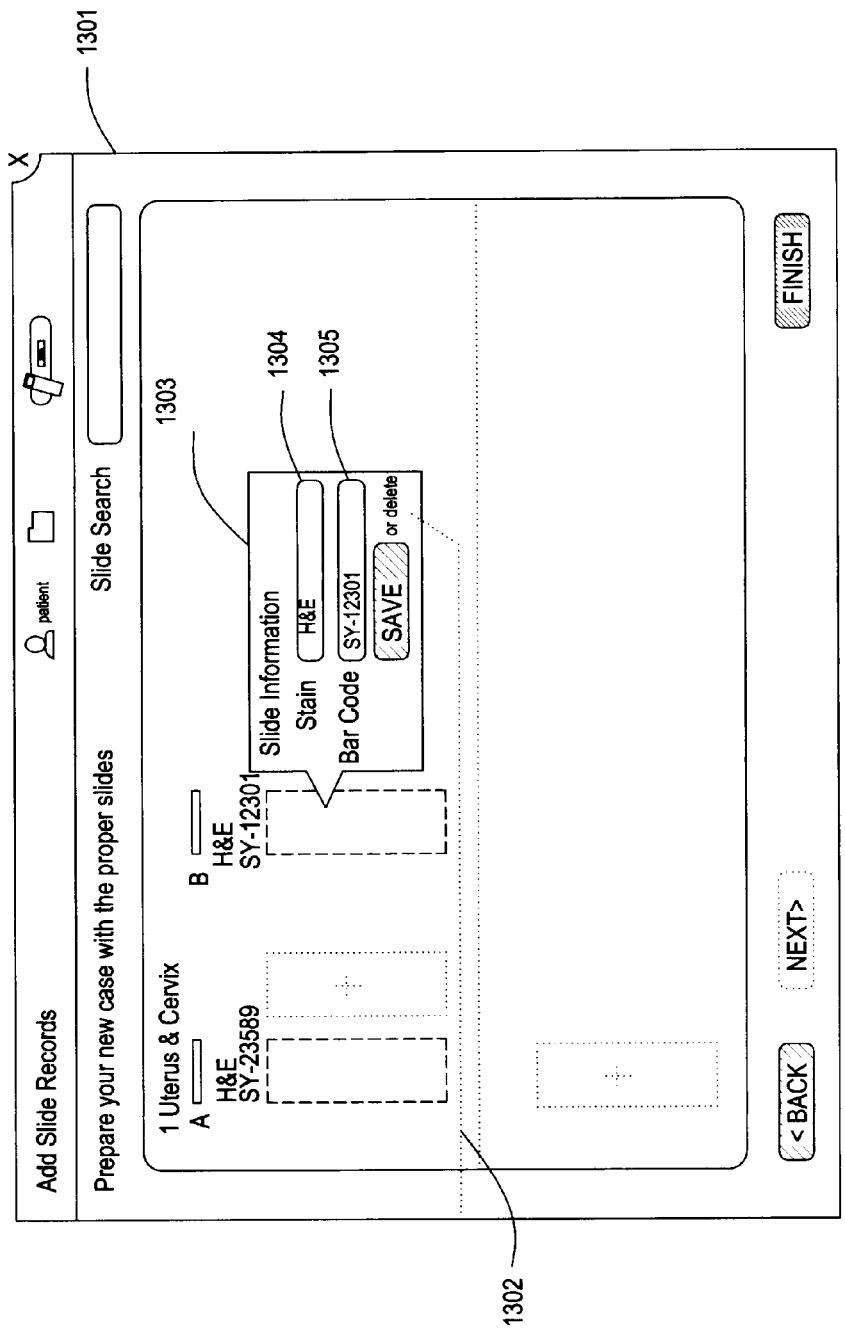
FIG. 13 provides an example of histology data entry.

Referring to FIG. 13, therein is depicted an example of histology data entry within the histology workflow management system arranged according to an embodiment. A histology data entry screen 1301 provides functionality for data entry. In the example illustrated in FIG. 13, the data entry screen 1301 is active in entering part, block, and slide record data; however, other types of data entry are also contemplated herein. The data entry screen 1301 may present one or more data entry elements, including slide records 1302. A user may select a data entry element, such as the slide record 1302 shown in FIG. 13, and access a slide information interface 1303. The slide information interface 1303 provides access to elements available for data entry. In the example of FIG. 13, stain 1304 and bar-code elements 1305 are available for data entry. Embodiments provide that any relevant information related to a data entry element may be accessible from a data entry interface, such as the image information interface 1303 in FIG. 13. Illustrative and non-restrictive examples of data entry elements include parts, blocks, stains, and slides organized into a slide tray by part or block.

Figure 14:
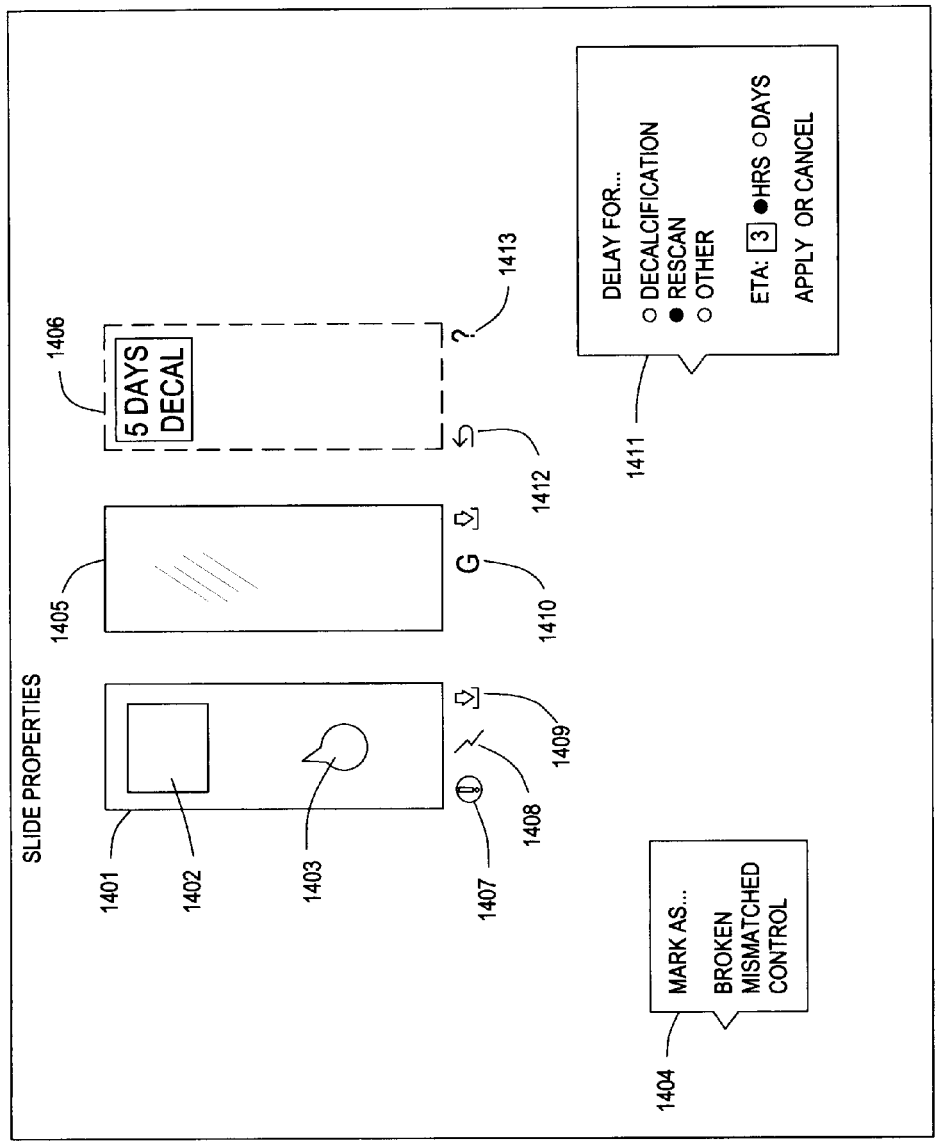
FIG. 14 provides an example physical slide, digital specimen image, and delayed slide record.

Slides and digital specimen images may be comprised of certain properties configured according to embodiments. FIG. 14 illustrates an example physical slide indicator, digital specimen image, and delayed slide record according to an embodiment. A digital slide or digital specimen image 1401 may be comprised of slide label 1402, tissue image 1403, and slide actions 1404, while delayed slide records 1406 may contain a delay property 1411 specifying the reason for and length of the delay. In addition, certain demarcations may be associated with a digital slide 1401, physical slide indicator 1405, or delayed slide record 1406. According to embodiments, a physical slide indicator 1405 may be configured to represent certain physical glass slides within the histology workflow management system. A non-limiting example provides that the physical slide indicator 1405 may represent a slide sent as glass only, thus forming a "sent as glass only" slide record. Non-limiting examples of demarcations illustrated in FIG. 14 include whether the slide has a scan issue 1407, is broken 1408, has been sent 1409 (e.g., to the pathologist), should be sent as glass 1410 (with or without sending the corresponding digital specimen image), requires rescan 1412, or is unmatched 1413.

According to embodiments, functions may be matched to slides, digital specimen images, or delayed slide records based on status. For example, if a user selects a digital specimen image demarcated as having scanning issues, certain functions may be active which may not be available if a user selects a digital specimen image demarcated as being unmatched. As such, the histology workflow management system may be configured according to embodiments to account for which type of slide or image has been selected so that the appropriate functions may be activated or made available. Continuing the example, selecting the digital specimen image with scanning issues may activate functions including, but not limited to, deleting the slide, sending the associated physical slide, sending the image, rescanning, or some combination thereof. On the other hand, selecting the unmatched digital specimen image may activate functions associated with matching the slide with a case or patient.

Figure 15:
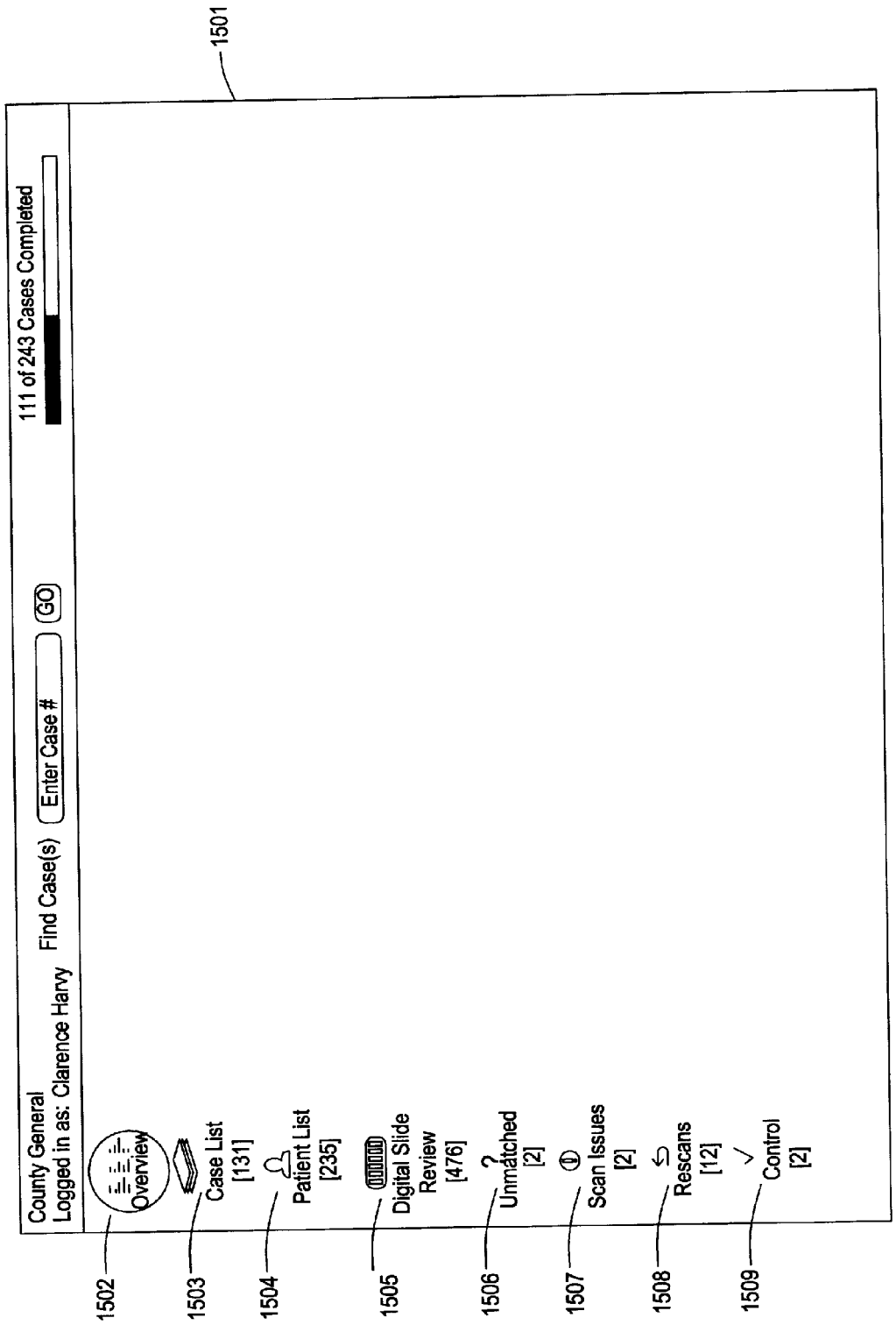
FIG. 15 provides an example of a high-level navigation configuration within the histology workflow management system.

Referring to FIG. 15, therein is provided an example of a high-level navigation configuration within the histology workflow management system according to an embodiment. A navigation user interface 1501 may be provided for presenting navigation operations, including navigation to screens and interfaces described previously herein. An overview 1502 function may provide a view across benches that depicts the workflow within the histology laboratory in real-time and ensures that the benches are receiving adequate workflow. A view of cases may be accessible from a case list 1503 function, including the ability to drill down to an individual case view. A list of patients may be accessible from the navigation user interface 1501 through a patient list 1504 function. A digital slide review 1505 navigation option may allow the placement of scanned slides into a queue for review, for example, by a histologist or laboratory technician. Slides or digital specimen images which have not been matched may be viewed through an unmatched 1506 function, while slides or digital specimen images with scan issues may be accessed through a scan issues 1507 function. Certain slides may require rescanning, which generally requires finding and pulling physical slides in the case trays. A list of such slides may be accessed from the navigation interface 1501 through a rescans 1508 function. In addition, control slides may be identified and filed within the histology workflow management system using the control 1509 function.

Figure 16:
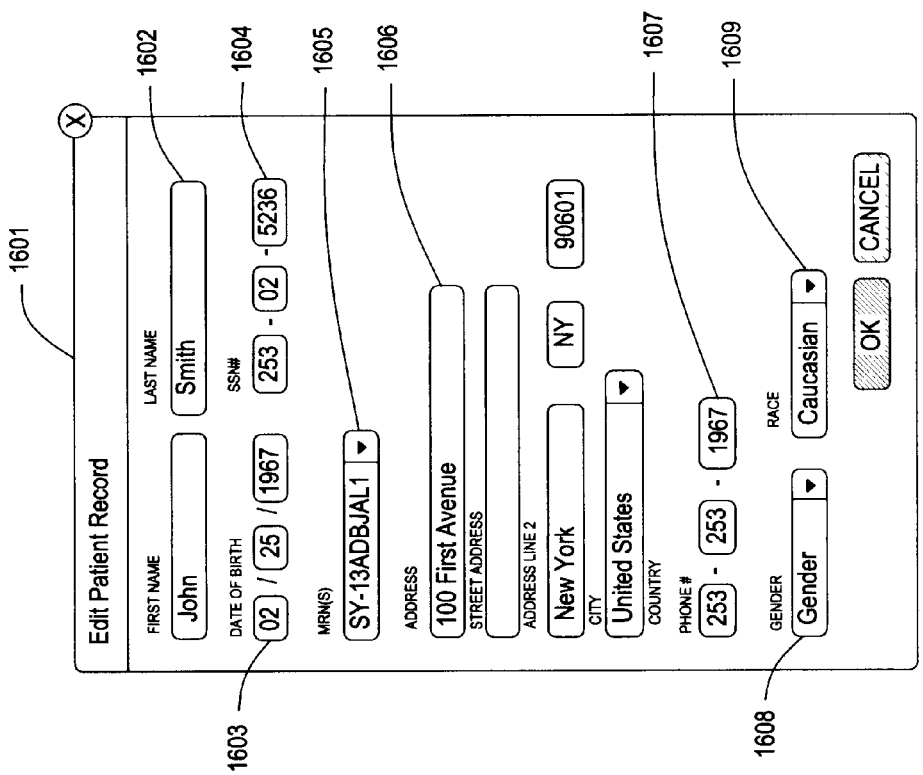
FIG. 16 provides an example user interface for creating a patient record.

Patient records may be generated and edited within the histology workflow management system. FIG. 16 provides an example user interface for creating a patient record according to an embodiment. The same or a similar interface may be used to edit existing patient records within the system. As shown in FIG. 16, a patient record may be comprised of a set of attributes accessible from a patient record interface 1601. Illustrative and non-restrictive examples of attributes include name 1602, date of birth 1603, social security number 1604, associated case or record numbers 1605, address 1606, phone number 1607, gender 1608, and race 1609.

Figure 17:
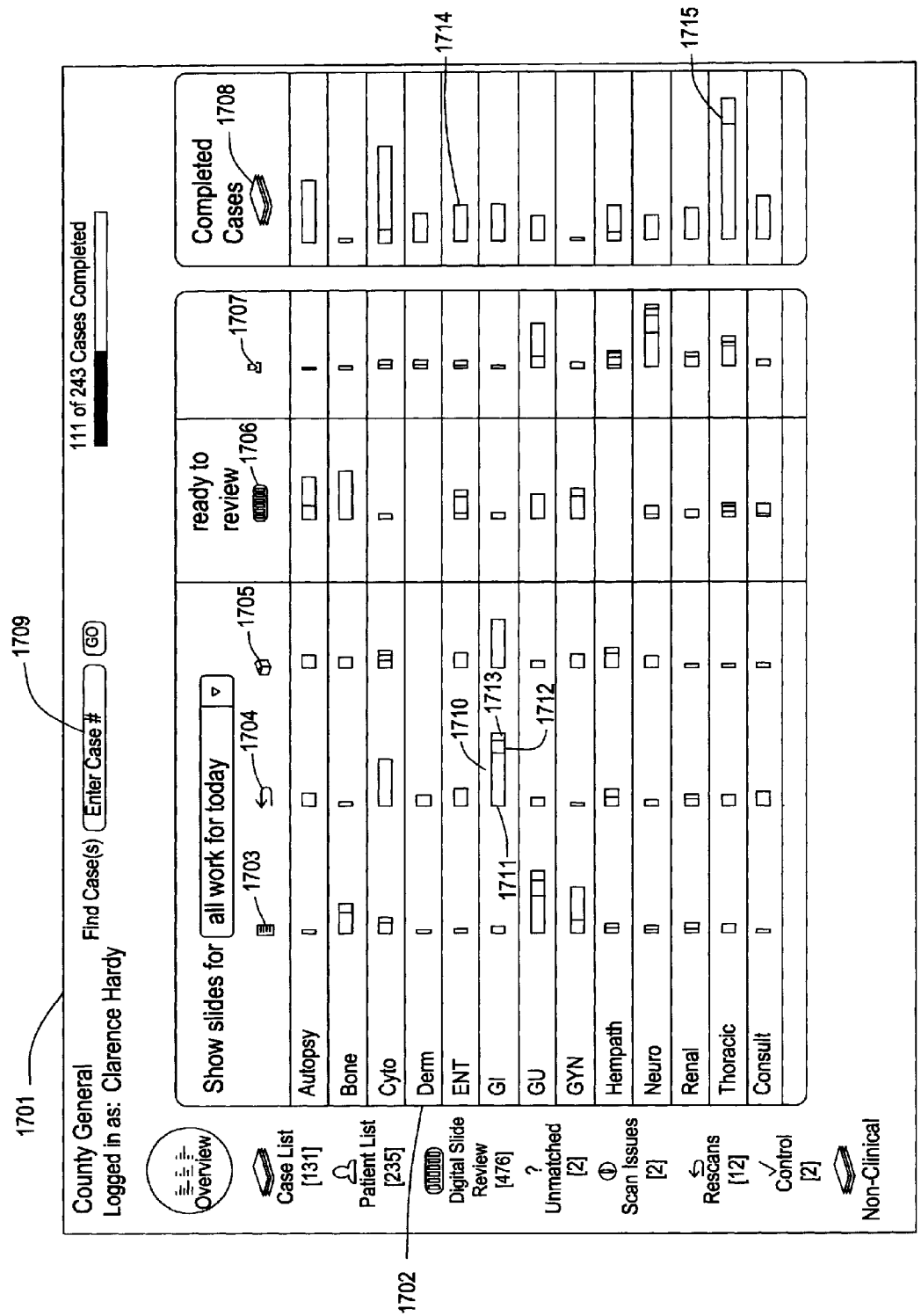
FIG. 17 provides an example user interface for histology workflow activity.

Scheduling and managing workflow are important functions in a histology laboratory environment. Performing such functions effectively requires current information, including the status of active cases, bench or laboratory workloads, and quality control outcomes. Embodiments provide for the presentation of histology workflow activity. Referring to FIG. 17, therein is provided an example user interface for histology workflow activity according to an embodiment. The histology workflow activity user interface 1701 presents activity elements for a set of entities. In the example of FIG. 17, the entities are benches or laboratories 1702. An illustrative and non-restrictive set of visualized activities includes slides ordered but not yet scanned 1703, rescans 1704, slides in the scanner 1705, ready to review 1706, slides that have been sent (e.g., to a pathologist) 1707, and completed cases 1708.

The number of slides at each bench or laboratory 1702 may be indicated visually, such as through the use of a bar 1710 or other display element. In addition, the number of slides 1710 may be further differentiated based on certain slide characteristics. In the example depicted in FIG. 17, the number of slides 1710 may be segmented into the stain type, such as H&E 1711, IHC 1712, and specials 1713; however, embodiments are not so limited, as the number of slides may be segmented based on any applicable characteristic (e.g., pathologist, facility, etc.). As with other user interfaces in the histology workflow management system configured according to embodiments, such as the case list user interface depicted in FIG. 8, slides may be filtered 1709. Non-limiting examples of filter categories include filtering based on date or status, such as stat, rush, routine, or same day request status. The histology workflow activity user interface 1701 aggregates data from various sources such as laboratories, pathologists, and histology workstations and presents a unified visualization to users. As a result, a user may have a comprehensive view of the histology workflow and may plan and schedule accordingly.

For example, a user may see that a first pathologist has received a certain number of cases, many of which have not been completed 1714, while a second pathologist has completed all of the cases she has been sent 1715. As such, the second pathologist may be ready to receive pending cases, while the first pathologist should not be sent a case until more of his cases are completed.

According to an embodiment, system records may be automatically generated based on integration of digital specimen image data and information system (e.g., LIS, APLIS) data. Non-limiting examples of records include case, patient, slide, and image records. Embodiments provide that a digital specimen image may be accessed within the histology workflow management system and automatically associated with available LIS data, for example, to build a case record within the system. LIS data associated with the digital specimen image may be used to populate attributes, including, but not limited to, data, identifying information, slides, images, or files, that make up a case. In a particular embodiment, the digital specimen image may be bar-coded and the information contained in the bar-code may be used to locate and match data in an information system accessible from the histology workflow management system; however, other sources of data and data matching, for example, RFID information, that may function to achieve a similar result are also contemplated herein.

Figure 18:
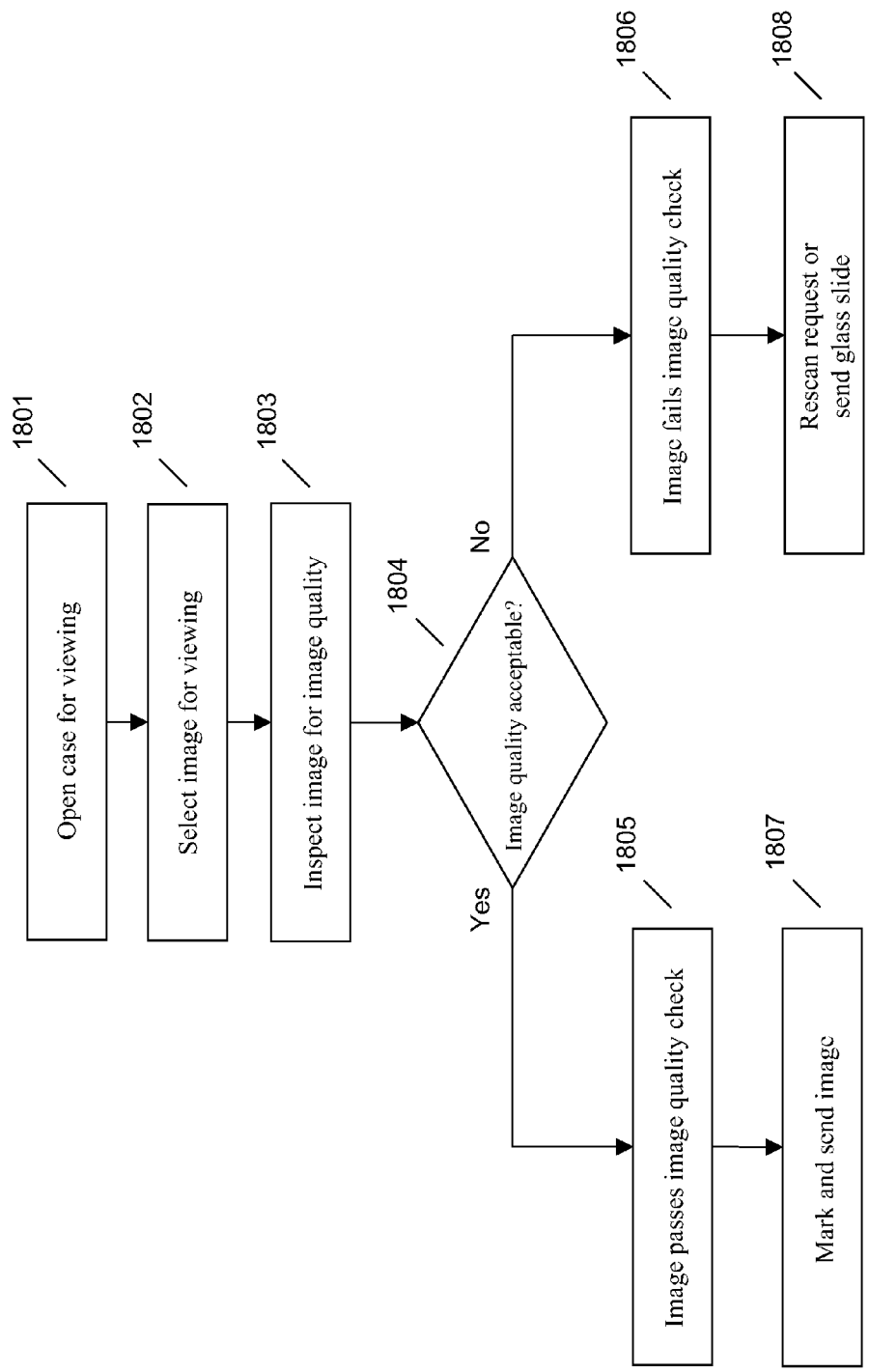
FIG. 18 provides an example image quality assurance check process.

As described previously, embodiments provide for quality assurance checks within the histology workflow management system, including image quality, image-to-case, tissue-to-block, and case completeness checks. Referring to FIG. 18, therein is provided an example image quality assurance check process configured according to an embodiment. A user may open a case 1801 for viewing, for example, in a slide tray viewer displaying all of the associated case information, slides, and digital specimen images. An image may be selected for viewing 1802 in a histology workflow management system viewer, such as a micro-image viewer. The image is inspected for image quality 1803, for example, to determine whether the image is a precise and accurate digital reproduction of the scanned tissue and for image characteristics such as stain quality. If the image quality is determined to be acceptable 1804, it has passed the image quality assurance check 1805; otherwise, it has failed the image quality assurance check 1806. If the image has passed, the image may be marked within the system as such or may be sent to a pathologist for review 1807, for example, by initiating a send image function. If the image has failed 1806, a rescan request function may be initiated for the associated slide or an indicator may be set to send the glass slide 1808, either with or without a digital image.

Figure 19:
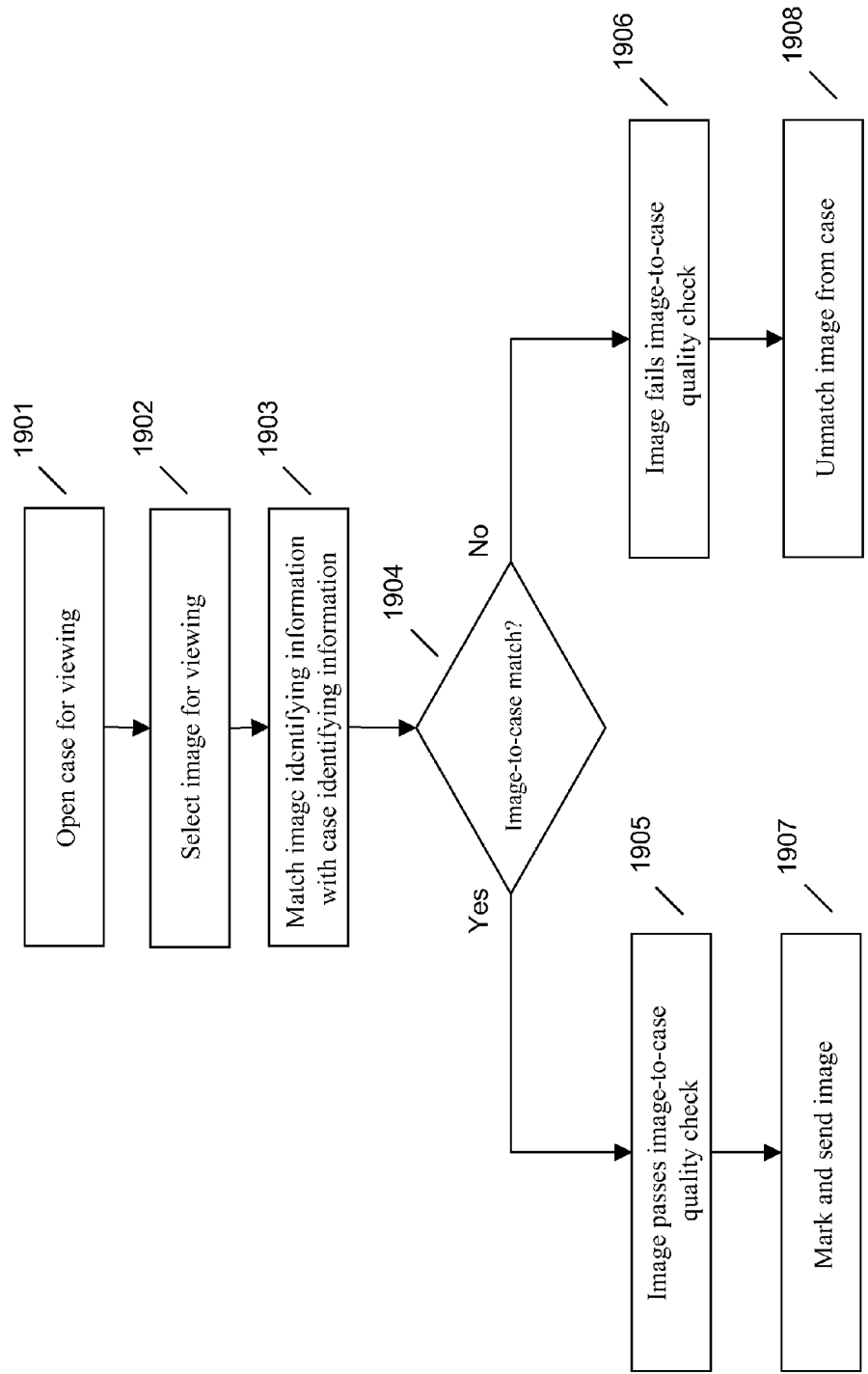
FIG. 19 provides an example image-to-case match quality assurance check process.

In FIG. 19, therein is provided an example image-to-case match quality assurance check process arranged according to an embodiment. A user may view a case 1901 and associated information, slides, and digital specimen images, for example, in a case viewer interface. An image may be opened 1902 in a viewer interface. Identifying information on the digital specimen image must match the corresponding identifying information for the case 1903. For example, the accession number on the digital specimen image must match the accession number for the case and the information on the slide label must match the label on the associated slide. If the identifying information matches 1904, the digital specimen image has passed the image-to-case match quality assurance test 1905; otherwise, it has failed 1906. If the case has failed 1906, embodiments provide functions for unmatching or deleting the image from the case 1908. If the image has passed 1905, a marking function may mark the image as such or a send image function may be initiated 1907, for example to send the image to a pathologist for viewing 1907.

Figure 20:
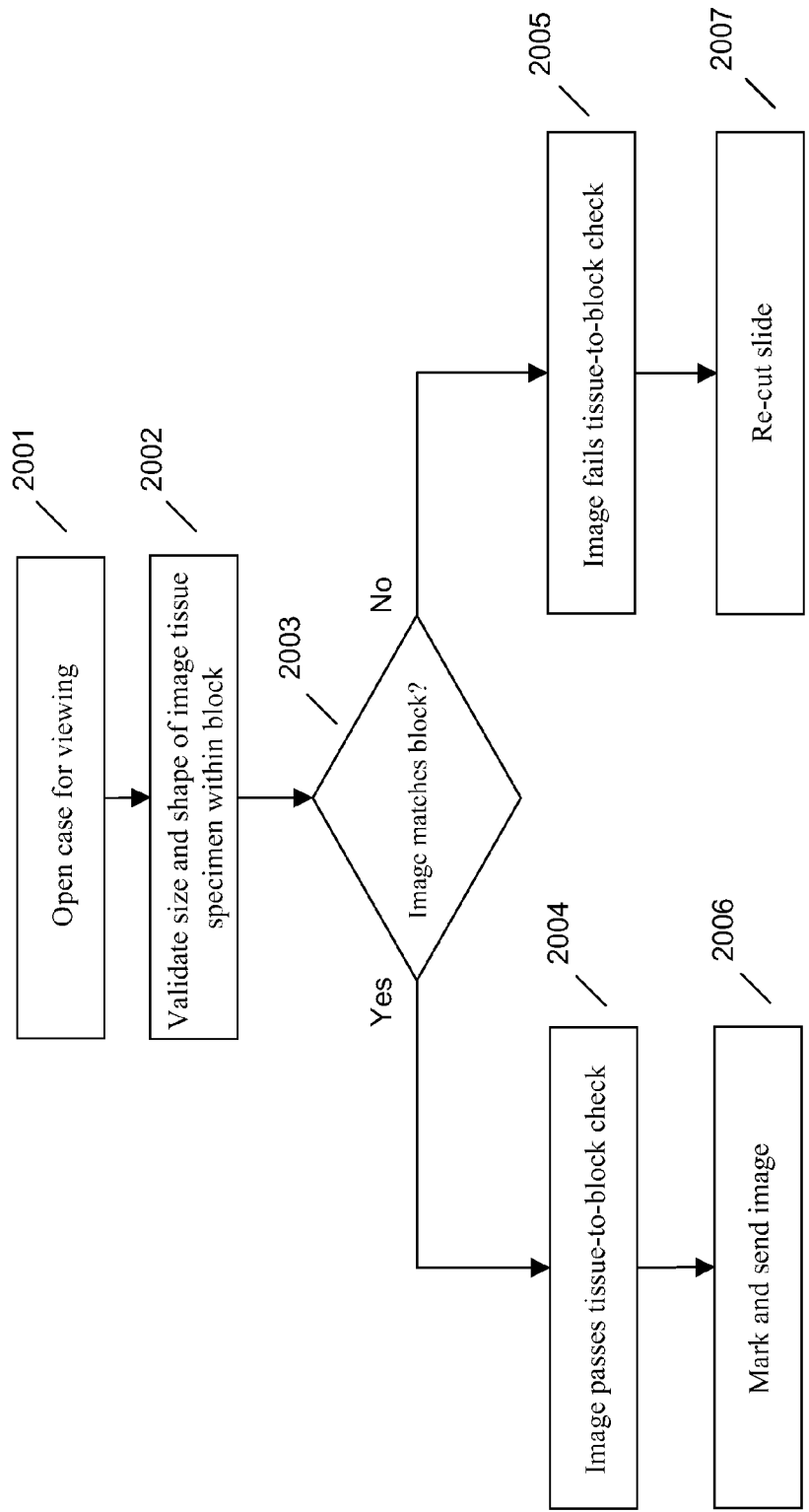
FIG. 20 provides an example tissue-to-block quality assurance check process.

FIG. 20 provides an example tissue-to-block quality assurance check process configured according to an embodiment. A case is selected for viewing in a slide tray viewer interface 2001, displaying all of the case information entered for the case, including, but not limited to, parts, blocks, slides, delay placeholders, and digital specimen slides. Images are inspected to validate the size and shape of the tissue across digital specimen images within a block 2002, for example, by comparing the tissue specimens on the digital specimen images to each other or to the physical slide. If the size and shape of the tissue for the digital specimen image matches the size and shape of the block 2003, it has passed the tissue-to-block quality assurance check 2004; otherwise, it has failed 2005. If the digital specimen image has passed 2004, a marking function may mark the image as such or a send image function may be initiated 2006, for example, to send the image to a pathologist for viewing 2006. If the digital specimen image has failed 2005, a function may be activated from the appropriate user interface to initiate a request to re-cut the slide 2007.

Figure 21:
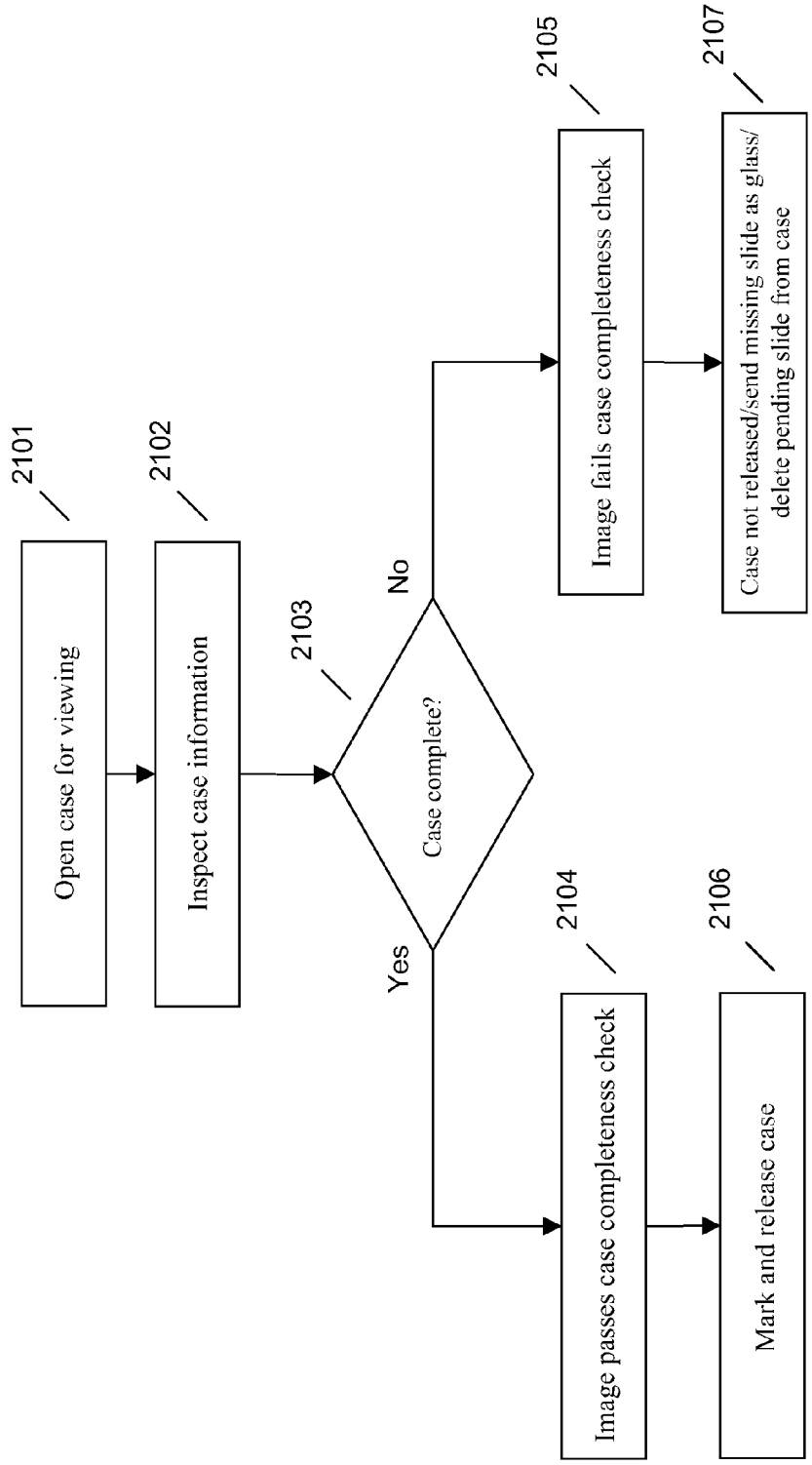
FIG. 21 provides an example case completeness quality assurance check process.

An example case completeness quality assurance check process arranged according to an embodiment is provided in FIG. 21. A case may be opened in a case viewer interface 2101, such as a slide tray viewer configured according to embodiments, which displays relevant case information, including accession number, parts, blocks, slides, and digital specimen images. All case information is inspected 2102 to ensure that the case is complete, for example, that all required information, slides, digital specimen images (e.g., no delay placeholders), parts, and blocks are present. If all of the required case information is present and correct 2103, the case passes the case completeness quality assurance check 2104; otherwise, the case fails the case completeness quality assurance check 2105. Exemplary reasons for failure 2105 may include a digital specimen image marked as delayed, or the presence of a placeholder for a slide that has not been scanned. If the case has passed 2104, a marking function may mark the case as such and the case may be released 2106, for example, through a release case function activated from a user interface. If the case has failed 2105, a user may elect to not release the case, activate a function requesting that missing slides be sent as glass, or initiate a function deleting certain pending slides from the case 2107.

Figure 22:
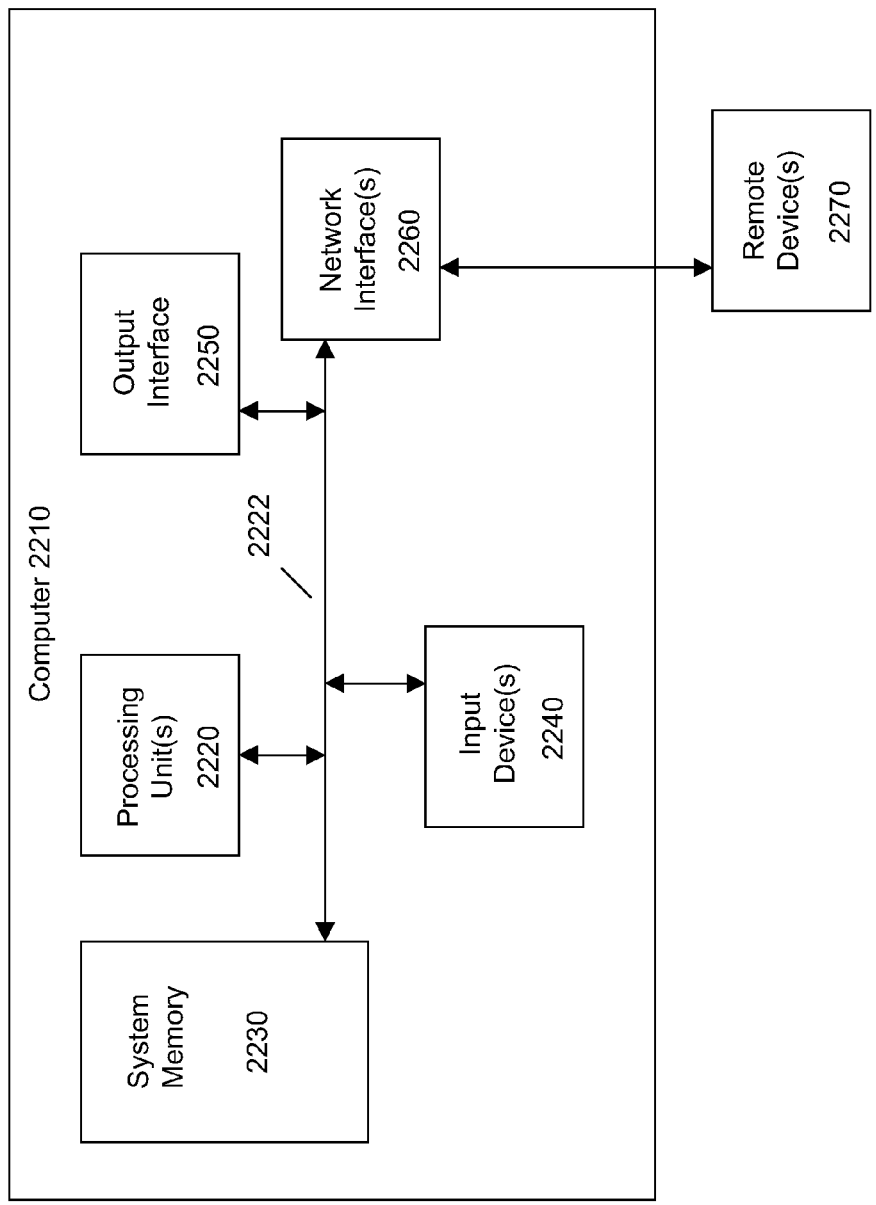
FIG. 22 illustrates an example circuitry of a computer system.

Referring to FIG. 22, it will be readily understood that certain embodiments can be implemented using any of a wide variety of devices or combinations of devices. An example device that may be used in implementing one or more embodiments includes a computing device in the form of a computer 2210.

Components of computer 2210 may include, but are not limited to, a processing unit 2220, a system memory 2230, and a system bus 2222 that couples various system components including the system memory 2230 to the processing unit 2220. The computer 2210 may include or have access to a variety of computer readable media. The system memory 2230 may include computer readable storage media in the form of volatile and/or nonvolatile memory such as read only memory (ROM) and/or random access memory (RAM). By way of example, and not limitation, system memory 2230 may also include an operating system, application programs, other program modules, and program data.

A user can interface with (for example, enter commands and information) the computer 2210 through input devices 2240. A monitor or other type of device can also be connected to the system bus 2222 via an interface, such as an output interface 2250. In addition to a monitor, computers may also include other peripheral output devices. The computer 2210 may operate in a networked or distributed environment using logical connections to one or more other remote computers or databases. The logical connections may include a network, such local area network (LAN) or a wide area network (WAN), but may also include other networks/buses.

It should be noted as well that certain embodiments may be implemented as a system, method or computer program product. Accordingly, aspects may take the form of an entirely hardware embodiment, an entirely software embodiment (including firmware, resident software, micro-code, et cetera) or an embodiment combining software and hardware aspects that may all generally be referred to herein as a "circuit," "module" or "system." Furthermore, aspects may take the form of a computer program product embodied in one or more computer readable medium(s) having computer readable program code embodied therewith.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, et cetera, or any suitable combination of the foregoing.

Computer program code for carrying out operations for various aspects may be written in any combination of one or more programming languages, including an object oriented programming language such as Java™, Smalltalk, C++ or the like and conventional procedural programming languages, such as the "C" programming language or similar programming languages. The program code may execute entirely on a single computer (device), partly on a single computer, as a stand-alone software package, partly on single computer and partly on a remote computer or entirely on a remote computer or server. In the latter scenario, the remote computer may be connected to another computer through any type of network, including a local area network (LAN) or a wide area network (WAN), or the connection may be made for example through the Internet using an Internet Service Provider.

Aspects are described herein with reference to flowchart illustrations and/or block diagrams of methods, apparatuses (systems) and computer program products according to example embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Although illustrated example embodiments have been described herein with reference to the accompanying drawings, it is to be understood that embodiments are not limited to those precise example embodiments, and that various other changes and modifications may be affected therein by one skilled in the art without departing from the scope or spirit of the disclosure.

What is claimed is:

1. A system for managing a histology operation, wherein:
   biological specimens of successive patient cases are collected, each of the cases containing specimens extracted from a single patient, the specimens being subjected to sequences of histological operations as requisitioned in each said case to enable examination of the specimens by a pathologist, and mounted on slides;
   including an imaging system operable to collect digital specimen images including images of glass slides bearing mounted specimens, the imaging system being operable to store the digital specimen images as files in a digital image memory;
   one or more processors;
   a memory in operative connection with the one or more of the processors;
   wherein, responsive to execution of program instructions accessible to the one or more processors, the one or more processors are configured to:
   access one or more patient records and one or more case records to which the digital specimen images relate;
   access one or more of said digital specimen images to match the one or more of said digital specimen images to the one or more case records based on one or more image properties of the one or more digital specimen images so as to associate respective ones of the digital specimen images with cases for presentation on a user display as an image of a set of glass slides that meet the requisitioned histological operations; and
   facilitate one or more image review functions comprising image quality assessment, case matching to associate the digital specimen images with said single patient and case completeness functions to associate the digital specimen images in each said case with corresponding said requisitioned operations.

2. The system according to claim 1, wherein the one or more image properties comprise an accession number, an image label, a stain type, and a match status.

3. The system according to claim 1, wherein the one or more image properties comprise an identifier for the digital specimen images.

4. The system according to claim 3, wherein the identifier comprises at least one of a barcode and an RFID element.

5. The system according to claim 3, wherein the one or more digital specimen images are matched with one of the one or more case records via the identifier.

6. The system according to claim 2, wherein the one or more image properties comprise a delay status, the delay status comprising whether an image is delayed in specimen preparation and imaging, reasons for the delay in specimen preparation and imaging, and an estimated time of arrival.

7. The system according to claim 1, wherein the one or more processors are further configured for generating case records, comprising the one or more processors obtaining information from one or more laboratory information systems in data communication with the one or more processors.

8. The system according to claim 2, wherein the match status of a digital specimen image is set to unmatched by the one or more processors pending identification of a matching case record for the digital specimen image by the user.

9. The system according to claim 8, wherein the one or more processors are further configured with add new case record and search case records functions that are activated by the one or more processors responsive to the match status of one of the images of the glass slides being unmatched.

10. The system according to claim 1, wherein the case matching image review function is supported by presenting an accession number of a digital specimen image directly adjacent to an image label of the digital specimen image.

11. The system according to claim 1, wherein the one or more processors are further configured with re-scan and send glass only functions that are activated during one or more image review functions.

12. The system according to claim 1, wherein a send image function is activated responsive to facilitate one or more image review functions.

13. The system according to claim 1, wherein the one or more processors are further configured to identify one or more of the histological operations requisitioned for the specimens, the requisitioned operations affecting the image properties of said biological specimen image.

14. A method for histology workflow management, comprising:
preparing biological specimens of patient cases for review by a pathologist, in sequences of connected operations as requisitioned, that are specific to single patients from whom the specimens are extracted and presented as sections from respective tissue blocks, mounting the specimens on glass slides, collecting digital specimen images including images of the glass slides bearing mounted specimens, and storing the digital specimen images to include images of the glass slides, as files in a digital image memory for presentation on a user display, wherein the images of the glass slides have distinct image properties;
accessing one or more of the digital specimen images;
matching the one or more of the digital specimen images to one or more case records for a single one of the patients based on one or more of the image properties of the one or more digital specimen images, the case records including the requisitioned operations and the requisitioned operations affecting the image properties of said digital specimen images; and
facilitating image review functions comprising image quality assessment, case matching to associate the images with said single one of the patients, tissue block matching to associate the images a same one of said tissue blocks, and case completeness functions to associate the images with all of said requisitioned operations.

15. The method according to claim 14, wherein the one or more image properties comprise an accession number, an image label, a stain type, and a match status.

16. The method according to claim 14, wherein the one or more image properties comprise an identifier for the digital specimen images.

17. The method according to claim 16, wherein the identifier comprises a barcode and an RFID element.

18. The method according to claim 16, wherein the one or more digital specimen images are matched with one of the one or more case records via the identifier at least in part by select, add/remove, move and edit operations effected by a user via the user display, on the images of the glass slides.

19. The method according to claim 15, wherein the one or more image properties comprise a delay status, the delay status comprising whether an image is delayed in specimen preparation and imaging, reasons for the delay in specimen preparation and imaging, and an estimated time of arrival.

20. The method according to claim 14, further comprising generating case records, including obtaining information from one or more laboratory information systems.

21. The method according to claim 15, wherein the match status of a digital specimen image is set to unmatched responsive to not locating a matching case record for the digital specimen image.

22. The method according to claim 21, further comprising add new case record and search case records functions that are activated responsive to the match status being set to unmatched.

23. The method according to claim 14, wherein the case matching image review function is supported by presenting an accession number of a digital specimen image directly adjacent to an image label of the digital specimen image.

24. The method according to claim 14, further comprising re-scan and send glass only functions that are activated during one or more image review functions.

25. The method according to claim 14, wherein a send image function is activated responsive to facilitate one or more image review functions.

26. The method according to claim 14, further comprising presenting one or more activity elements.

27. The method according to claim 26, wherein the one or more activity elements comprise sent slides, re-scans, and completed cases.

28. A histology operation for managing preparation and presentation digital images of biological specimens for viewing, comprising:
a specimen collection and preparation operation wherein biological specimens of successive patient cases are collected, each of the patient cases containing specimens from a single patient, the specimens being subjected to sequences of histological operations as requisitioned in each said case to enable examination of the specimens, and mounted on slides;
an imaging system operable to collect digital specimen images including images of glass slides bearing mounted specimens, the imaging system being operable to store the digital specimen images as files in a digital image memory;

one or more processors;

a memory in operative connection with the one or more of the processors;

wherein, responsive to execution of program instructions accessible to the one or more processors, the one or more processors are configured to:

access one or more patient records and one or more case records to which the digital specimen images relate;

access one or more of said digital specimen images and to match the one or more of said digital specimen images to the one or more case records based on one or more image properties of the one or more digital specimen images so as to associate respective ones of the digital specimen images with cases for presentation on a user display as an image of a set of glass slides that meet the requisitioned histological operations; and facilitate one or more image review functions comprising image quality assessment, case matching to associate the digital specimen images with said single patient, tissue block matching to associate with one another the digital specimen images taken from a same tissue block, and case completeness functions to associate the digital specimen images with corresponding said requisitioned operations.

29. The system of claim 1, wherein matching the one or more digital specimen images to the one or more case records based on one or more image properties of the one or more digital specimen images includes one of a select, add/remove, move and edit operation, effected by a user via the user display, on images of the glass slides that have not been matched by the one or more processors.

30. The method of claim 14, wherein the one or more image review functions includes manipulation by a user, on the user display, of the images of the glass slides.

31. The method of claim 30, wherein matching the one or more digital specimen images to the one or more case records based on one or more image properties of the one or more digital specimen images includes one of a select, add/remove, move and edit operation, effected by a user via the user display, on images of the glass slides that have not been matched by the one or more processors.

* * * * *